(12) United States Patent
Ting et al.

(10) Patent No.: US 9,995,661 B2
(45) Date of Patent: Jun. 12, 2018

(54) FLOW-THROUGH HIGH HYDROSTATIC PRESSURE MICROFLUIDIC SAMPLE PREPARATION DEVICE AND RELATED METHODS THEREFOR

(75) Inventors: Edmund Y. Ting, Kent, WA (US); Alexander Lazarev, Lexington, MA (US)

(73) Assignee: PRESSURE BIOSCIENCES, INC., South Easton, MA (US)

( * ) Notice: Subject to any disclaimer, the term of this patent is extended or adjusted under 35 U.S.C. 154(b) by 0 days. days.

(21) Appl. No.: 13/212,934

(22) Filed: Aug. 18, 2011

(65) Prior Publication Data

US 2012/0122705 A1 May 17, 2012

Related U.S. Application Data

(60) Provisional application No. 61/374,867, filed on Aug. 18, 2010.

(51) Int. Cl.
*G01N 1/00* (2006.01)
*G01N 1/28* (2006.01)
*G01N 35/10* (2006.01)

(52) U.S. Cl.
CPC ......... *G01N 1/286* (2013.01); *G01N 35/1095* (2013.01); *Y10T 436/25* (2015.01)

(58) Field of Classification Search
CPC .................. G01N 1/286; G01N 35/1095
USPC ............................................. 506/7
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 6,036,923 A | 3/2000 | Laugharn, Jr. et al. | |
| 6,120,985 A | 9/2000 | Laugharn, Jr. et al. | |
| 6,127,534 A | 10/2000 | Hess et al. | |
| 6,619,311 B2 | 9/2003 | O'Connor et al. | |
| 6,635,469 B1 | 10/2003 | Litt et al. | |
| 7,064,192 B2 | 6/2006 | Randolph et al. | |

(Continued)

FOREIGN PATENT DOCUMENTS

| | | | |
|---|---|---|---|
| EP | 0814900 B1 | | 9/2001 |
| WO | WO2008092102 | * | 7/2008 |

OTHER PUBLICATIONS

Erickson et al., Integrated Microfluidic Devices, 2004, Analytica Chemica Acta, 507, pp. 11-26.*

(Continued)

*Primary Examiner* — Karla A Dines
(74) *Attorney, Agent, or Firm* — Lando & Anastasi, LLP

(57) ABSTRACT

Described herein is a sample preparation device including a sample delivery source, an inline means of transferring the sample from the sample source into a deformable channel within a pressure vessel, and out of the channel into downstream analysis components, a deformable channel disposed within the pressure vessel, the deformable channel having an inlet end and an outlet end fluidly connectable to high pressure valves and a means to measure the fluid pressure within the deformable channel, an external source of a controlled pressurized fluid fluidly connectable to the pressure vessel and a controller system that monitors and controls the sample fluid pressure by control of the external pressure vessel fluid.

31 Claims, 7 Drawing Sheets

(56) References Cited

U.S. PATENT DOCUMENTS

| | | | |
|---|---|---|---|
| 2002/0125424 A1* | 9/2002 | Ellson | H01J 49/0454 |
| | | | 250/288 |
| 2002/0137157 A1 | 9/2002 | Randolph et al. | |
| 2003/0083475 A1 | 5/2003 | Randolph et al. | |
| 2004/0038333 A1 | 2/2004 | Randolph et al. | |
| 2006/0188970 A1 | 8/2006 | Randolph et al. | |
| 2006/0212068 A1* | 9/2006 | Boylan et al. | 606/200 |
| 2007/0092632 A1 | 4/2007 | Kubow et al. | |
| 2008/0060802 A1* | 3/2008 | Breglio et al. | 166/162 |
| 2008/0300386 A1 | 12/2008 | Lazarev et al. | |
| 2009/0203068 A1 | 8/2009 | Lopez-Ferrer | |
| 2009/0215194 A1* | 8/2009 | Magni | B01L 3/502707 |
| | | | 436/174 |

OTHER PUBLICATIONS

Brown et al., Oak Ridge National Laboratory, High Pressure Ion-Exchange Column Design for Remote Hot Cell Operation, 1974, p. 1-11.*

Rudert et al., 1976, American Mineralogist, vol. 61, pp. 1012-1015.*

International search report for PCT/US2011/048302 dated Dec. 6, 2011.

* cited by examiner

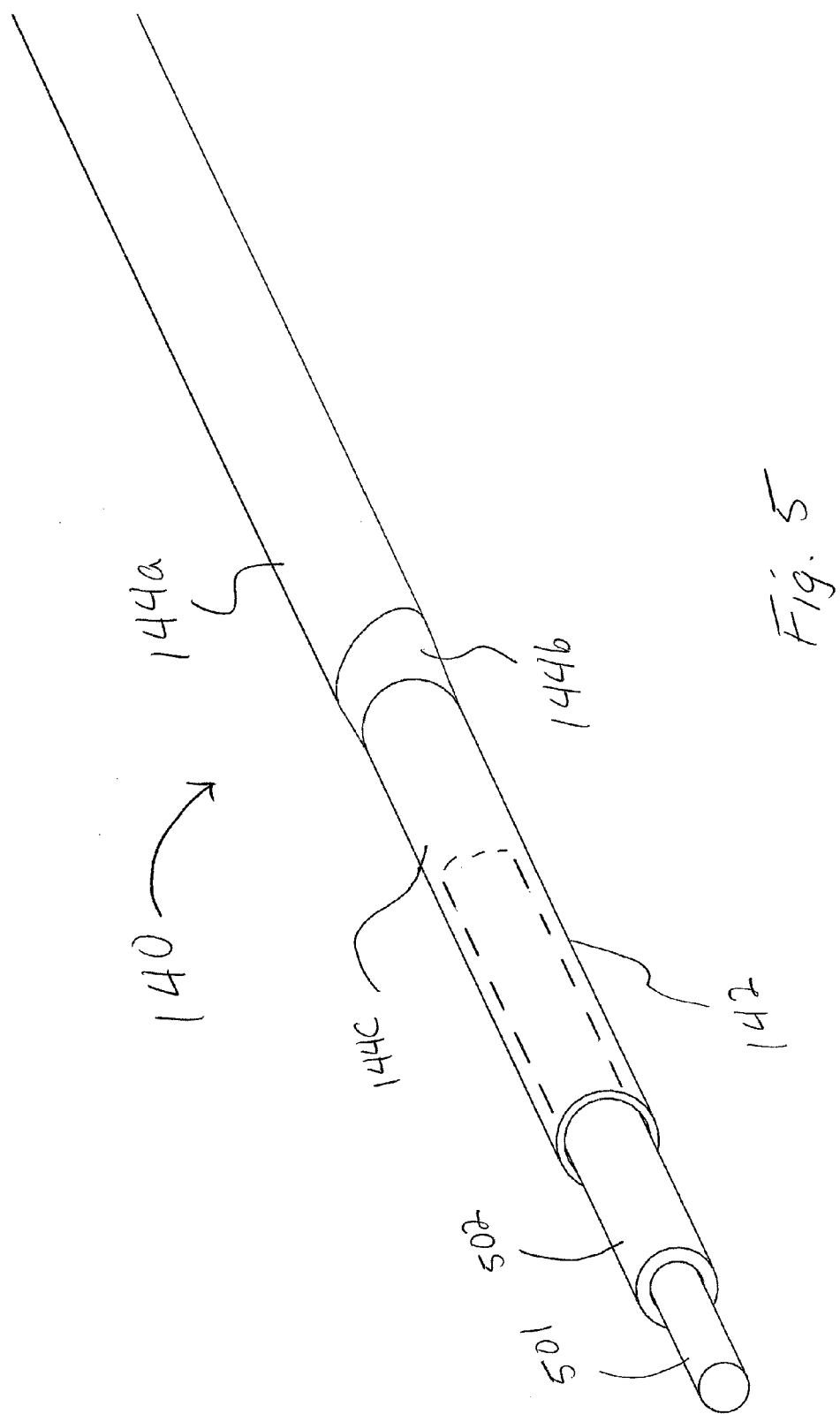

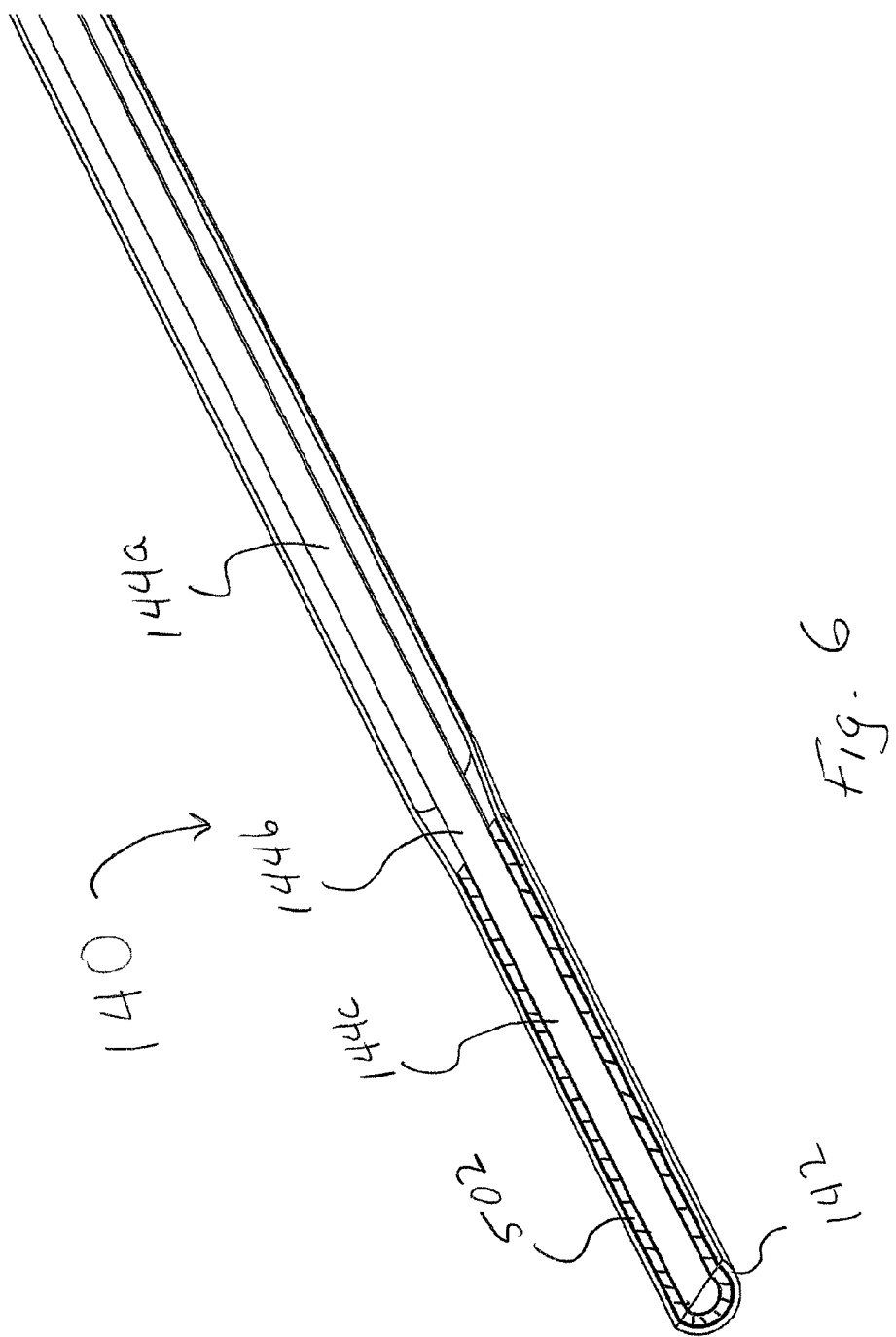

FLOW-THROUGH HIGH HYDROSTATIC PRESSURE MICROFLUIDIC SAMPLE PREPARATION DEVICE AND RELATED METHODS THEREFOR

CROSS REFERENCE TO RELATED APPLICATIONS

This application claims priority under 35 U.S.C. § 119(e) to U.S. Provisional Application Ser. No. 61/374,867 entitled "FLOW-THROUGH HIGH HYDROSTATIC PRESSURE MICROFLUIDIC SAMPLE PREPARATION DEVICE AND RELATED METHODS THEREFOR," filed Aug. 18, 2010, which is incorporated herein by reference in its entirety.

BACKGROUND OF INVENTION

1. Field of Invention

This invention relates to systems and methods, chemical and biological analysis and, in particular, to systems, apparatus, and methods of sample preparation and conditioning involving integrated high hydrostatic pressure treatment with flow-through analytical systems and methods that facilitate separation or extraction or chemical reaction of components of a sample.

2. Discussion of Related Art

Advancements in chemical and biological analysis have been driven by analytical and separation equipment. However, the first step in analytical processes, sample preparation, has received little attention and has predominantly focused on off-line traditional mechanical shearing or chemical approaches at various temperatures. Most analytical instruments require true solutions of the analytes as an input, while most samples, particularly biological and environmental samples, contain cells, tissues, suspensions, emulsions and other heterogeneous compositions. The majority of published methods combine modern state-of-the-art high sensitivity and high resolution analytical methods with the legacy sample preparation steps. Most sample preparation protocols commonly used have been developed before modern molecular analysis methods, such as mass spectrometry, DNA sequencing and PCR amplification techniques, existed. Many sample preparation methods in common use continue to rely on traditional techniques such as mechanical homogenization, ultrasonic cavitational disruption, grinding of frozen samples in liquid nitrogen, etc. Most of these techniques require processing samples one-by-one in a dedicated container, leading to the necessity of manual sample handling or the use of robotic liquid handlers. Sample transfer typically presents a risk of undesired sample loss, potential for operator error, sample cross-contamination, and overall lack of an automated in-line process from initial sample to results.

Thermodynamic control of molecular interactions and chemical equilibria could be accomplished by varying the two orthogonal parameters of temperature and pressure. Temperature has been by far the most widely used perturbation in biochemical thermodynamics. However, a complete thermodynamic response can be utilized by using pressure perturbations, which is governed by different thermodynamic effects than temperature.

Hydrostatic pressure has been used to promote cell lysis, extraction and partitioning of various molecular entities as exemplarily illustrated by Lazarev et al. in U.S. Patent Application Publication No. 2008/0300386 A1, which is incorporated herein by reference in its entirety for all purposes. The control of molecular interactions has also been disclosed as noted by Litt et al. in U.S. Pat. No. 6,635,469 B1, which is also incorporated herein by reference in its entirety for all purposes. Enzymatic reactions, including proteolysis for preanalytical sample preparation in mass spectrometry-based proteomics have also been disclosed by, for example, Laugharn et al. in European Patent Specification No. EP 0 814 900 B1, which is incorporated herein by reference in its entirety for all purposes, and by Lopez-Ferrer in U.S. Patent Application Publication No. 2009/0203068 A1. To date, the application of hydrostatic pressure to liquid samples has been predominantly achieved by pressurizing samples contained in closed pressure vessels. Such techniques may not be practical for pressurization of very small volume liquid samples in the micro liter range and do not interface well with automated analysis systems.

Flow-through high pressure reactor apparatus has been described by Laugharn et al. in U.S. Pat. No. 6,036,923, which is incorporated herein by reference in its entirety for all purposes, which allows loading and unloading operations to be automated by the use of the high-pressure valves to trap the sample in a segment of the tubular flow path, enabling a variety of applications, ranging from chromatography at high pressure to control of enzyme kinetics under pressure. The design of the reactor described above may not accommodate miniaturization and the volumes of samples which could be pressurized has remained relatively large (1 ml and above). The alternative method of pressurization of small samples has also been described by, for example, Lopez-Ferrer in U.S. Patent Application Publication No. 2009/0203068 A1. However, such approach is limited in a way that the sample material is placed in direct contact with the liquid used as a source of hydrostatic pressure through the series of valves, and which poses the risk of sample cross-contamination when processing of samples is conducted in a serial fashion. Furthermore such approaches can only be pressurized to the maximum pressure level available on the LC system and the sample pressure cannot be easily controlled to slowly ramp or rapidly cycle pressure as a function of time.

SUMMARY OF THE INVENTION

One aspect of the present invention relates to a sample preparation device comprising a sample source; a pressure vessel having a pressurizing valve fluidly connectable to a source of pressurizing fluid and a pressure relieving valve; a flexible channel disposed within the pressure vessel, the flexible channel having an inlet end fluidly connectable to the sample source and an outlet end; a source of a pressurized fluid fluidly connectable to an inlet of the pressure vessel through a first valve; a controller system configured to generate a pressurizing signal that actuates the pressurizing valve and regulate the pressure of the fluid within the pressure vessel. In some configurations of the sample preparation device, the pressure within the vessel is sufficient to deform the deformable channel and pressurize the deformable channel and transmit pressure to its contents by means of flexible deformation of the said channel.

Another aspect of the present invention relates to a method of sample preparation. The method can comprise introducing a sample within a deformable channel disposed within a pressure vessel; fluidly isolating the sample within the deformable channel; increasing the pressure of a pressurizing fluid within the pressure vessel to a pressure sufficient to deform the deformable channel; reducing the pressure of the pressurizing fluid within the pressure vessel;

allowing the deformable channel to relax back to the pre-deformed condition, and withdrawing the fluid from the deformable channel. Some cases of the method of sample preparation can further comprise repeatedly increasing and reducing the pressure of the pressurizing fluid to effect pressure cycling of the sample within the deformable channel. Further cases of the method of sample preparation can further comprise analyzing the components of the pressure cycled sample. Analysis, for example, can involve utilizing any one or more of immobilization, chromatography, and extraction.

A further aspect of the present invention relates to a computer-readable medium including computer-readable signals stored thereon defining instructions that, as a result of being executed by a computer, instruct the computer to perform a method of sample preparation, the method comprising introducing a sample within a deformable channel disposed within a pressure vessel; fluidly isolating the sample within the deformable channel; increasing the pressure of a pressurizing fluid within the pressure vessel to a pressure sufficient to deform the deformable channel; reducing the pressure of the pressurizing fluid within the pressure vessel; and withdrawing the fluid from the flexible channel.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing.

In the drawings:

FIG. 5 is a perspective view of a portion of a pressure transfer cell in accordance with another embodiment of the present invention;

FIG. 6 is a cross-sectional view of a portion of the pressure transfer cell illustrated in FIG. 5 comprising a deformed section and a non-deformed section.

DETAILED DESCRIPTION

Figure 1:
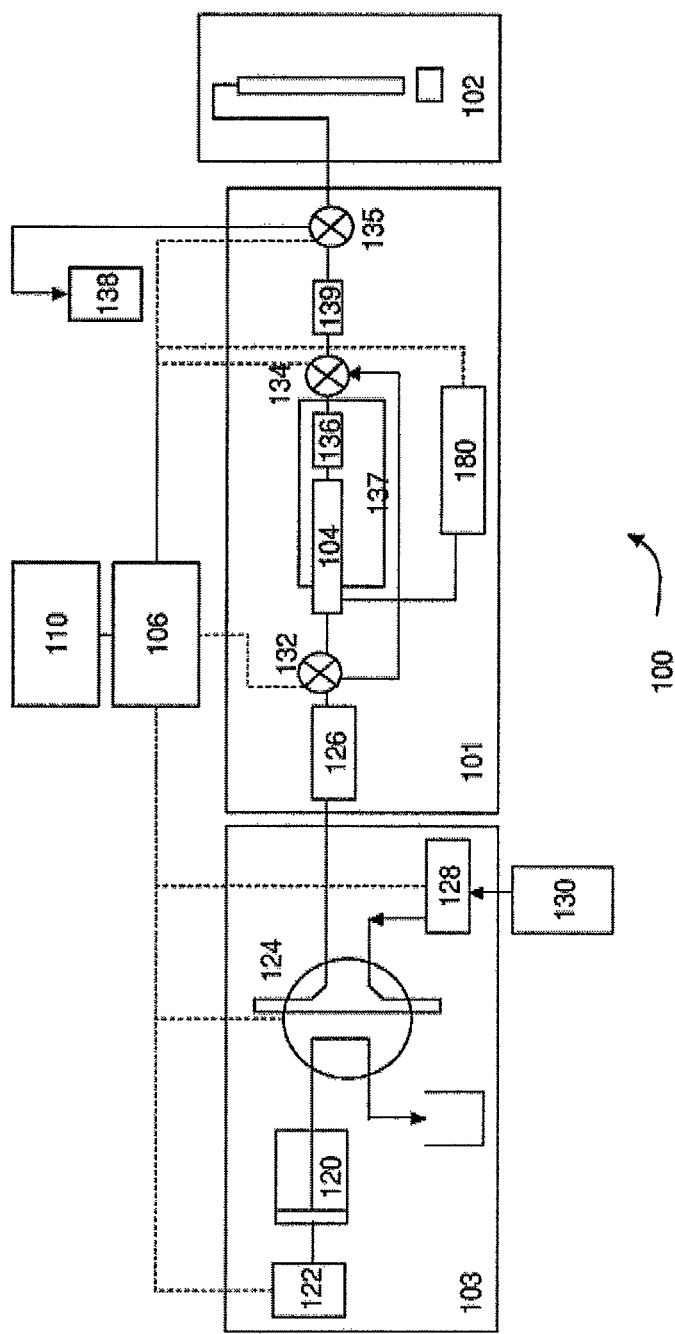
FIG. 1 is a schematic illustration of a portion of a pressure cycling apparatus in accordance with one or more embodiments of the invention.

The system and techniques of the present invention can be directed to continual or semi-continuous high pressure facilitated chemical synthesis, derivation, analysis, such as proteomic analysis, mass spectroscopy, labeling, such as stable isotopic labeling for mass spectroscopic analysis, fluorescent labeling, and tagging with ultraviolet-absorbing chromophores for high pressure liquid chromatography (HPLC). However, the various systems and techniques of the invention are not limited as such, and other applications relevant to pressure cycling sample preparation processes are contemplated (e.g., using the device as a source of pressure (for example, to push fluid into a separation column)). At least some aspects of the systems and techniques of the invention can be directed to modulating, facilitating, or effecting one or more reactions that can be at least partially pressure regulated by high pressure conditions in a sample mixture. One or more further aspects of the invention can involve pressurizing a sample mixture by increasing or decreasing an applied pressure thereto, quench a chemical or enzymatic reaction step, move a sample mixture into or from a subsystem or component to another component or subsystem, change the pH of the sample mixture, introduce one or more reagents that changes one or more characteristics of the sample mixture or initiates or terminates one or more reactions of one or more components of the sample mixture.

As used herein, a sample or a sample mixture can include one or more specimens, cultures, biological samples, and environmental samples from human and animal tissue as well as naturally occurring and synthetic materials. The sample mixture can include one or more organic compounds such as enzymes or enzyme substrates which are immobilized on surfaces wetted by the sample mixture. In some cases, however, the enzyme substrates can be suspended within the sample mixture.

The term sample vessel is used to indicate a container for enclosing the amount or volume of the sample or sample mixture within a chamber, channel, annulus, or volume. The sample vessel is not limited to any one geometrical configuration or design and can be a container in which one or more reactions may occur.

Non-limiting examples of organic compounds that may be present in the mixture include natural and synthetic nucleic acids, nucleotides, oligonucleotides, α-amino acids, oligo-peptides, peptidomimetics, depsi-peptides, peptides, saccharides, liposaccharides, and mixtures thereof. Organic compounds that can be present in the sample mixture also include radio-labeled compounds, and other compounds with detectable tags or signals. Non-limiting examples of the nucleotides that can be present as the one or more organic compounds include deoxynucleoside 5' triphosphates such as dATP, dCTP, dGTP, dTTP, and dUTP; dideoxynucleotides as well as nucleotides for resolving sequencing ambiguities such as $c^7$dGTP, dITP, and $c^7$dATP; 2'-deoxynucleoside-5'-O-(1-thiotriphosphates) such as dATPαS; 5-methyldeoxy-cytidine 5'-triphosphate; ribonucleoside 5'-triphosphates; 2'3'-ddNTPs; and 7-deaza 2'-dNTPs. Non-limiting examples of amino acids that can be present in the sample mixture include α-amino acids, Gly, Ala, Val, Leu, Ile, Ser, Thr, Asp, Asn, Lys, Glu, Gln, Arg, H is, Phe, Cys, Trp, Tyr, Met, and Pro; and other natural or synthetic amino acids such as norleucine, ethylglycine, ornithine, methylbutenylmethyl-threonine, phenylglycine, γ-carboxyglutaric acid, β-hydroxyproline, γ-hydroxyproline, δ-hydroxylysine, methylated amino acids, and ε-iodo, ε1-ε2-diiodo, ε-nitro-, ε-amino- and O-acetyl-tyrosine. Non-limiting examples of saccharides that can be present in the sample mixture include glucose, fructose, galactose, mannose, sucrose, and other substituted saccharides.

The sample mixture can also include ionized species such as inorganic or organic cationic or anionic species, non-limiting examples of which include lithium, sodium, potassium, magnesium, calcium, chromium, iron, manganese, zinc, cobalt, copper, and aluminum, fluoride, chloride, bromide, iodide, sulfate, phosphate, hydrogen phosphate, carbonate, and bicarbonate.

In some cases, the sample mixture can also include gases such as the noble gases, reactive gases such as HCl, HF, diatomic hydrogen, and diatomic halogen, and atmospheric gases such as carbon dioxide, carbon monoxide, and oxygen.

The sample mixture can include one or more solvents or mixture thereof such as methylene chloride, tetrahydrofuran, dimethyl formamide, ether, benzene, toluene, hexane, and ethyl acetate, ethyl alcohol, methyl alcohol, acetone, acetonitrile, trifluoroethanol, and 1.1.1.3.3.3-hexafluoro 2-propanol.

As used herein, a vector (or vehicle) is a nucleic acid molecule that transfers a DNA segment or segments from one cell to another. An expression vector is a recombinant DNA molecule containing a desired coding sequence and nucleic acid sequences necessary for the expression of the operably linked coding sequence in a particular host organism. Nucleic acid sequences for expression in procaryotes usually include a promoter, an optional operator, and a ribosome binding site. Eukaryotic cells are known to utilize promoters, enhancers, and termination and polyadenylation signals. Complementarity may be partial, wherein only some of the bases are matched according to the base pairing rules, or complete. The degree of complementarity between nucleic acid strands significantly affects the efficiency and strength of hybridization between nucleic acid strands. Complementarity therefore bears on the accuracy of amplification reactions, as well as detection methods dependent upon binding between nucleic acids. Hybridization is the pairing of complementary nucleic acids. Hybridization and the strength of hybridization, i.e., the strength of the association between the nucleic acids, is impacted by such factors such as the degree of complementary between the nucleic acids, stringency of the conditions involved, the $T_m$ of the formed hybrid, and the G:C ratio within the nucleic acids. $T_m$ is the melting temperature, or the temperature at which a population of double-stranded nucleic acid molecules becomes half dissociated into single strands. A simple estimate of the value of $T_m$ may be calculated by $$T_m=81.5+0.41(\% \ G+C),$$

when a nucleic acid is in aqueous solution at 1 M sodium chloride (NaCl), see e.g., Anderson and Young, Quantitative Filter Hybridization, in Nucleic Acid Hybridization (1985). Other references include more sophisticated calculations which take structural as well as sequence characteristics into account for the calculation of $T_m$. Stringency refers to the conditions of temperature, ionic strength, and the presence of other compounds such as organic solvents, under which nucleic acid hybridizations are conducted. Under high stringency conditions, nucleic acid base pairing will occur only between nucleic acid fragments that have a high frequency of complementary base sequences. Under weak or low stringency conditions, nucleic acids that are derived from organisms that are genetically diverse will occur, even though the frequency of complementary sequences is usually less.

As used herein, nucleic acid and nucleic acid substrate encompass DNA, RNA, and peptide nucleic acids (PNA), whether single stranded, double stranded, or a single strand with intermittent complementary segments, or combinations thereof. Chimeric oligonucleotides having stretches of both RNA and DNA residues on the same oligonucleotide are commercially available from, for example, oligos Etc., Inc., Wilsonville, Oreg. The present invention does not, in principle, limit the length of the nucleic acid; the nucleic acid may be genomic or a defined length, e.g. short oligonucleotides, or fragment thereof (including single bases). A nucleic acid may be obtained from any source and therefore may be naturally occurring; naturally occurring and purified; or produced synthetically, recombinantly, or by amplification. Nucleic acids include modified nucleic acids formed by an enzyme which removes a nucleotide from the nucleic acid substrate, or adds a chemical moiety, such as a terminal methyl group, or a linking group to bond the nucleic acid to another molecule. A nucleic acid may be immobilized on a polymer or composite bead, matrix, or other support surface. Nucleic acids may be amplified by any amplification method. Amplifiable nucleic acids typically include a sample template, which is typically a nucleic acid from a sample. A background template may or may not be present in the sample, and is typically an inadvertent result of carryover, or from nucleic acid contaminants sought to be purified away from the sample such as those from organisms other than those to be detected, analyzed, characterized, or reproduced may be present as background in a sample mixture. Non-limiting examples of amplification methods include polymerase chain reaction (PCR), such as the method for increasing the concentration of a segment of a target sequence in a mixture of genomic DNA without cloning or purification disclosed by K. B. Mullis in U.S. Pat. Nos. 4,683,195 and 4,683,202, which is hereby incorporated by reference.

Enzymatic activity typically depends on the temperature, pressure, and solvent system (solvent and salts). Typically, preferred enzymatic activity can be in a temperature in a range of from about 10° C. to about 80° C., and can be in a range of from about 25° C. to about 37° C. Optimal enzymatic temperatures can be readily ascertained by consulting with literature from, for example, New England BioLabs, Ipswich, Mass. A substantially inactive enzyme typically exhibits less than about 20%, and generally less than 10%, of its activity at optimum enzymatic temperature (and atmospheric pressure). Ideally, an inhibited or substantially inactive enzyme is completely inactive (0% activity) but determination thereof may be limited by the sensitivity and uncertainty of a given activity assay. A reversibly inhibited enzyme exhibits no activity under restrictive or inhibitory conditions but can resume activity when exposed to permissive conditions or elimination of the restrictive conditions. Typically, a pause or transition period can occur after permissive conditions are imposed, but before enzymatic activity resumes. Permissive conditions include those conditions under which optimum enzymatic activity occurs, and also those conditions under which slower, but measurably useful activity occurs. A primer is typically an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method. A probe is typically an oligonucleotide, occurring naturally as in a purified restriction digest or produced synthetically, which is capable of hybridizing to another oligonucleotide of interest. Probes can be useful in the detection, identification, and isolation of particular gene sequences. A probe, the particular gene sequence, or both, can be labeled with one or more reporter molecule, so that the probe, the particular gene sequence, or both, can be detectable by, for example, ELISA, as well as enzyme-based histochemical assays, fluorescent, radioactive, and luminescent detection systems. A target sequence is the region of nucleic acid bounded by the primers used for detection and/or amplification, e.g., by the polymerase chain reaction. Thus, it is desirable to identify the target from among other sequences. A segment is a region of nucleic acid within the target sequence.

A PCR product or amplification product is the resultant mixture of compounds after two or more cycles of the steps of denaturation, annealing, and extension. These terms encompass the case where there has been amplification of one or more segments of one or more target sequences. Amplification reagents are those reagents needed for amplification exclusive of primers, a nucleic acid template, and an amplification enzyme. Amplification reagents include deoxyribonucleoside triphosphates and buffer. Typically, amplification reagents and other reaction components are placed in a reaction, e.g., sample, vessel, e.g., test tube, microwell, pressure deformable casing with optional outlets, etc.

Restriction endonucleases and restriction enzymes refer to enzymes (e.g., bacterial enzymes), each of which cuts double-stranded DNA at or near a specific nucleotide sequence.

DNA molecules are said to have 5' ends and 3' ends because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide can be referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being upstream or 5' of the downstream or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, an oligonucleotide having a nucleotide sequence encoding a gene refers to a DNA sequence comprising the coding region of a gene or in other words the DNA sequence which encodes a gene product. The coding region may be present in either a cDNA or genomic DNA form. Suitable control elements such as enhancers/promoters, splice junctions, polyadenylation signals, etc., may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc., or a combination of both endogenous and exogenous control elements.

Enzymes that synthesize or digest polymer substrates may dissociate from the substrate after each catalytic event, i.e., they may be non-processive (coextensive with distributive). They may remain bound to the polymer until many cycles of reaction are completed, i.e., they may be processive.

One or more aspects of the invention can involve pressure cycling systems which produce rapid fluctuations in pressure applied to a sample mixture. The applied pressure fluctuations can have a plurality of pressure profiles. Where a fluctuation between two pressures, P and P', occurs, for example, one or more of the pressure profiles of the invention can include variations wherein the length of time that each of pressures P and P' is applied is the same; variations wherein the length of time at which pressure P is applied is greater than the length of time at which pressure P' is applied; variations wherein the transition time from pressure P to pressure P' is about the same as the transition time from pressure P' to pressure P; variations wherein the transition time from pressure P to pressure P' is longer than the transition time from pressure P' to pressure P; and variations wherein one or several pauses at one or more intermediate pressures during the transition from pressure P to pressure P'; and variations wherein a ramping rate from pressure P to pressure P' is equal to, greater, or less than a ramping rate from pressure P' to pressure P. Pressure fluctuation profiles may include more than two pressures P and P'.

One or more further aspects of the invention involve pressure cycling systems capable of adding and removing components within a chamber, channel, or volume while maintaining or even increasing the pressure applied thereto. Further features of the invention can involve addition of components to the sample mixture.

Some configurations of the pressure cycling systems of the present invention may be utilized in techniques or applications wherein at least one step of a reaction thereof is pressure-sensitive. Non-limiting examples of such techniques or applications include enzymatic, non-enzymatic, chemical, physical, kinetic, and thermodynamic reactions or wherein pressure-sensitive interactions which can involve covalent bond breaking and bond formation, non-covalent, ionic, hydrogen bonds, and van der Waals forces; hydrophobic or hydrophilic interactions; and structural modifications such as secondary, tertiary, and quaternary, i.e., folding, and formation of helices and sheets. Various aspects of the invention can involve modification or altering at least one characteristic, such as a rate of a reversibly pressure-sensitive reaction step. For example, one or more pressure-sensitive reactions that can be altered can include those that have a rate that can be decreased, stopped, increased, or started. Particular embodiments can thus involve changing from a characteristic inhibitory pressure to a characteristic permissive pressure.

In accordance with still further aspects of the invention, any of the systems and techniques described herein can further involve utilizing one or more incubation periods to promote or create one or more desirable conditions or to effect or promote one or more of conversion, transformation, and characterization of one or more components. The one or more incubation periods or events can involve maintaining any one of a pressurized, depressurized, cooling, and heating activities. The duration of any one or more of such activities can vary from about one second to about thirty minutes. In some cases, any of the one or more incubation periods can progress at changing conditions and is not limited to being performed at a steady or constant state. For example, any of the one or more periods can be performed while the temperature of the sample liquid is increasing or decreasing, preferably at a predetermined rate.

FIG. 1 exemplarily illustrates an embodiment of a pressure cycling system generally indicated at 100 pertinent to one or more aspects of the invention. The pressure cycling system 100 can comprise sample delivery 103, preparation 101, and analysis systems or trains 102. One or more sample delivery trains 103, coupled to one or more sample condition or preparation trains 101, typically coupled to one or more analytical trains 102. Each sample preparation train 101 typically comprises one or more pressure transfer cells 104 that can pressurize a sample to high hydrostatic pressures, of from about 2,000 psi to about 10,000 psi, or to about 50,000 psi, or even to about 100,000 psi, but in some cases, in a range of from about 2,000 psi to about 100,000 psi. Some preferred configurations of pressure transfer cell 104 can expose at least a portion of the sample to be evaluated to such high pressures, or pressurize the at least a portion of the sample to static high pressures or dynamic pressurization conditions. Further, in some embodiments, at least one of the one or more pressure transfer cells 104 can dynamically pressurize the at least a portion of the sample thereby exposing or pressurizing the at least a portion of the sample to cyclic pressurization operations. Cyclic pressurization can be performed periodically, aperiodically, or asymmetrically. Cyclic pressurization can also be performed under progressively increasing pressurization conditions or under progressively decreasing pressurization conditions.

Sample delivery train 103 can include one or more sample injection or introduction apparatus 120 disposed to introduce a specific, predetermined amount, e.g., volume, of the sample into at least one of the one or more pressure transfer cells 104. Injection apparatus 120 can comprise, for example, an actuator 122 that can displace a piston for dispensing the sample mixture contained in a chamber thereof. Sample preparation train 101 can utilize one or more valve assemblies 124, such as a HPLC rotary valve, to direct at least a portion of the sample mixture from injection apparatus 120 into one or more of the pressure transfer cells 104. Valve assembly 124 typically comprises a plurality of ports, optionally at least two of such ports fluidly connected through one or more external flow loops. A controller 106 of a control system can be utilized to generate at least one control or output signal that energizes or actuates actuator 122 to dispense at least a portion of the sample mixture within injection apparatus 120 and introduce into valve assembly 124. Controller 106 can also be configured to generate another output or control signal that appropriately displaces an actuator (not shown) to position valve assembly 124 to receive or load the at least a portion of sample mixture from apparatus 120, typically through one or more ports thereof. Valve assembly 124 can be configured or oriented to effect fluid communication between injection apparatus 120 and pressure transfer cell 104 thereby allowing introduction of the at least a portion of the sample mixture from injection apparatus 120 into transfer cell 104 upon activation of actuator 122.

In some cases, sample conditioning train 101 can comprise one or more of a first or pre-separation apparatus 126 that effects at least partially, separation of one or more components of the sample mixture before introduction thereof into one or more of any of the pressure transfer cells 104. Separation apparatus 126 can comprise one or more affinity-based separation devices such as those that utilize antibody columns. Typically one or more mobile phases or eluents would be utilized to effect motility of the sample mixture or components thereof through the one or more first separation apparatus 126. In such instances, a pump 128 may be utilized to withdraw the mobile phase from one or more reservoirs 130 and introduce mobile phase into separation apparatus 126 through valve assembly 124.

Sample conditioning train 101 can further comprise a first or inlet isolation valve 132 that fluidly isolates an inlet of pressure transfer cell 104, and a second or outlet isolation valve 134 that fluidly isolates an outlet of pressure transfer cell 104. One or more cartridge traps 136 (in some embodiments, these traps are also referred to as reactors) may be utilized to facilitate further conditioning of one or more components of the sample mixture. For example, trap 136 can comprise a fritted assembly or a perforated plate apparatus that can effect lysing. As exemplarily illustrated, a cartridge trap 136 is utilized downstream from the one or more pressure transfer cells 104 but one or more traps may be implemented, serially or in parallel, upstream of or downstream from pressure transfer cell 104.

One or more temperature regulation devices, such as heaters 137 or thermoelectric coolers, can also be utilized before, during, or after the one or more pressurizing or depressurizing events in accordance with one or more aspects of the present invention.

A plurality of cartridge filters may be also utilized. For example, a filter may be utilized upstream of separation apparatus 126 to prevent large-sized particulate components from being introduced thereinto.

FIG. 1 further illustrates an optional bypass line fluidly connecting valves 132 and 134, around the one or more pressure transfer cells 104. Preferably, controller 106 can be configured to generate a valve actuation signal to effect orientation of one or more of both valves 132 and 134 appropriately. The pressure of the sample mixture can be monitored by the control system and used in a feed back loop to control the working or pressurizing fluid pressure so that desired sample cell pressure is achieved.

Undesirable material can be disposed at container 138.

If a plurality of separation devices 126 are utilized, each or one or more can be arranged sequentially or in parallel flow paths.

Figure 2:
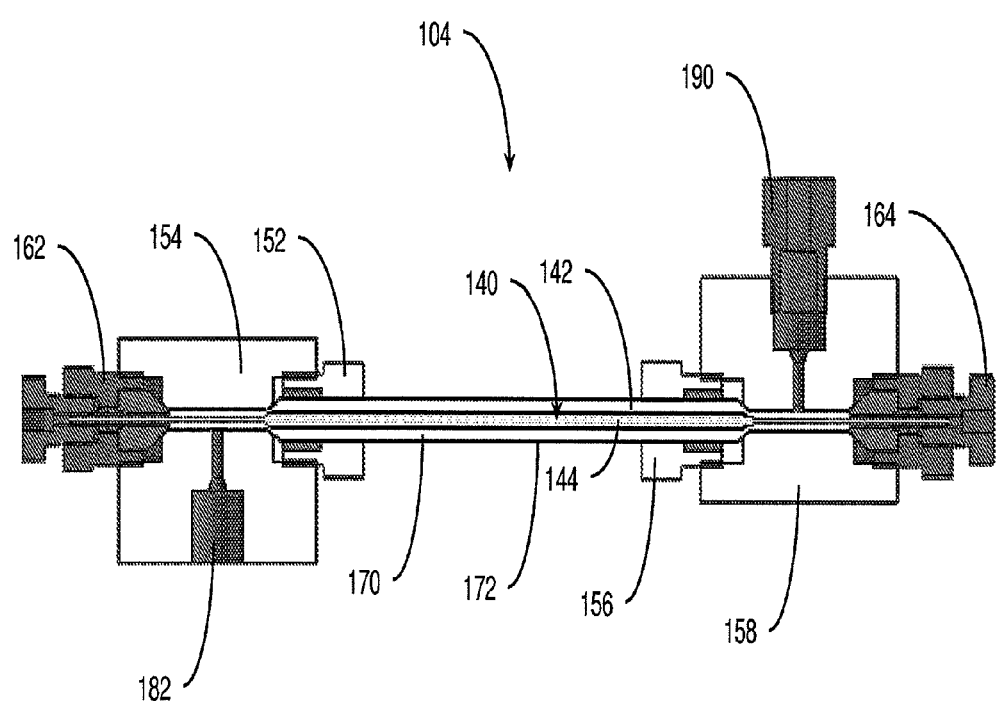
FIG. 2 is a cross-sectional view of a flow path of a pressure transfer cell for sample preparation and analysis in accordance with one or more embodiments of the invention.
Figure 3:
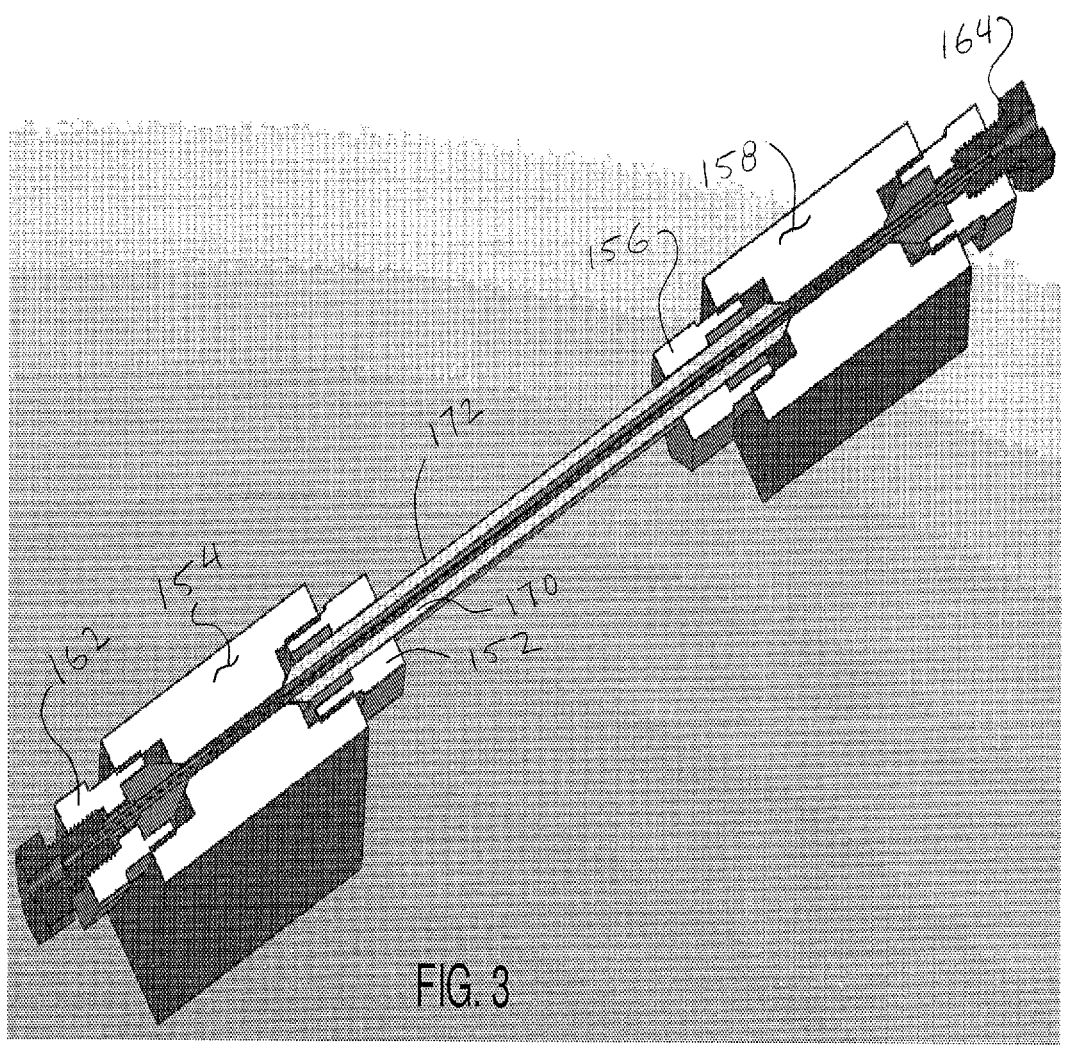
FIG. 3 is an alternative perspective cross-sectional view of the flow path of the pressure transfer cell for sample preparation and analysis of FIG. 2.

As exemplarily illustrated in FIGS. 2 and 3, pressure transfer cell 104 can include a first chamber, such as sample chamber 140, having a wall 142 defining a channel 144 for containing the sample mixture. Wall 142 can be made from a polymeric material, e.g., polyethylene. Preferably wall 142 is comprised of a flexible or deformable material so that first chamber 140 serves as a flexible channel. Other materials that can be utilized as wall 142 include, for example, other polymeric materials such as PEEK or FEP; or metallic materials such as stainless steel, titanium alloys, or superelastic NiTi alloys. The surface, or portions thereof, may be inert, nonbinding, hydrophilic, or hydrophobic.

The thickness of wall 142 can vary along the length of channel 144 to allow preferential deformation in sections of channel 144 upon exposure to pressurizing fluid in pressure chamber 170. For example, the thickness of wall 142 can be greater at one or both terminal ends of wall 142 forming channel 144, e.g., ends corresponding in length to about 5% or about 10% of the overall length of channel 144. In further configurations, the wall 142 forming channel 144 can have portions thereof comprising Ni-clad PEEK tubing and portions without such cladding. For example, the terminal ends of the wall forming the channel may be clad with Nickel and the portion of the channel 144 therebetween left unclad. The clad portion will enable the sealing of the inner tube by the use of compression fittings. The unclad portion will be easily deformed by the chamber pressure in order to transfer pressure into the sample fluid.

The wall 142 forming the channel 144 can have any geometric cross-sectional configuration. Thus, although illustrated in FIG. 2 to have a circular cross-section, channel 144 or portions of channel 144 can have a deformed (e.g., ellipsoidal or other geometric orientation the creates a more flexible wall to enhance movement as understood by one of skill in the art) cross-sectional geometry. Such an arrangement can promote channel deformation in a predictable mode. Such an ellipsoidal geometry is illustrated in FIGS. 5 and 6.

Figure 5A:
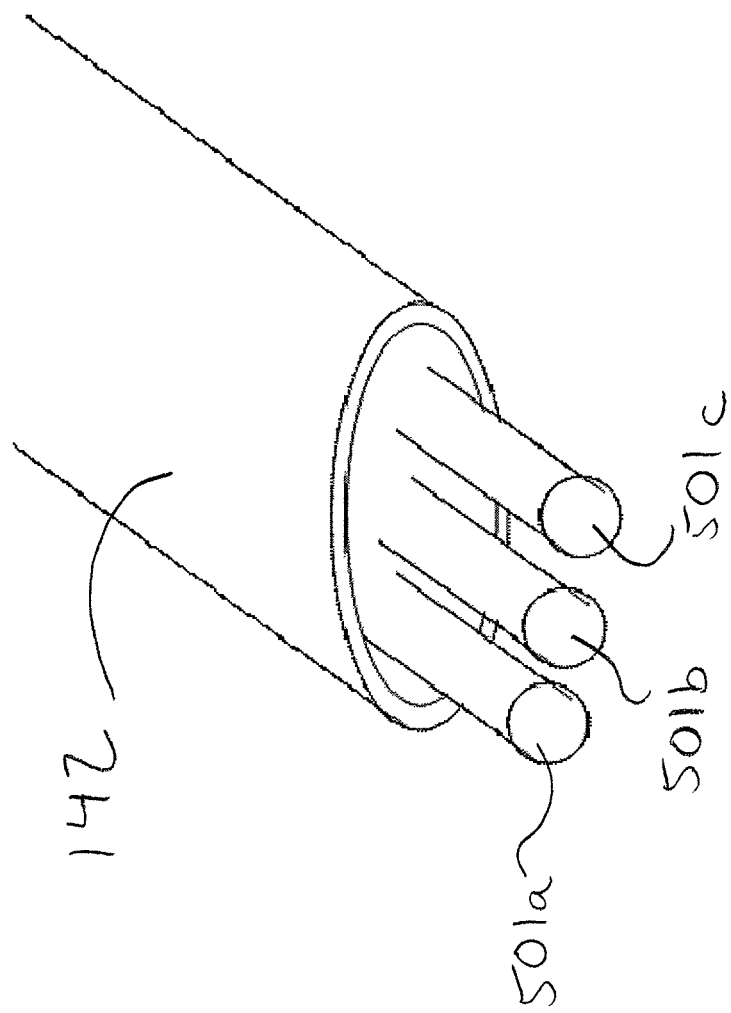
FIG. 5A is a perspective view of a portion of a pressure transfer cell in accordance with another embodiment of the present invention that includes three filler rods.

In some embodiments, described in detail with respect to FIGS. 5 and 6 below, the channel 144 can contain one or more filler rods (e.g., 1, 2, 3, 4, etc.) disposed within the channel 144. For example, in one embodiment depicted in FIG. 5A, the channel 144 includes three filler rods 501a, 501b, 501c. The one or more filler rods may extend along a length of the channel 144 to the terminal ends of the channel, or may extend only along a central portion of the length of the channel 144 that does not extend to the terminal ends of the channel. The one or more filler rods are preferably formed from substantially incompressible materials, such as stainless steel, that are more incompressible than the sample mixture to be contained within the sample chamber 140. Preferably, the material from which the one or more filler rods are formed is inert, nonbinding, hydrophilic, or hydrophobic. The presence of one or more filler rods effectively reduces the internal volume of the channel 144, thereby permitting any deformation or deflection of the channel wall 142 to generate a higher pressure than if the one or more filler rods were not present. Because less deformation or deflection of the channel wall 142 is needed to generate higher pressures, the pressure transfer cell can be expected to last through more pressure cycles, due to a lesser amount of structural fatigue to the wall 142 during each pressure cycle. It should be appreciated that the presence of one or more filler rods can reduce the amount of flexing of the pressure transfer cell without altering the flexibility of the channel wall 142

In some embodiments, wall 142 can be surrounded by an external brace (not shown). When surrounded by a brace and when wall 142 is pressurized internally, the wall 142 expands and rests on the external brace. In some embodiments, this external brace can allow for a more highly elastic material for forming the channel 144. An external brace feature allows for the channel 144 to achieve greater flexibility without concern for bursting due to high internal pressures. In some embodiments, the brace is perforated, meshed, webbed or comprises any other design which allows the brace to maintain the support necessary for the channel 144 to resist bursting under high internal pressures. As discussed further below, one or more filler rods may be used to limit compression of the channel 144, and to reduce the volume of the channel. The pressure of the sample mixture can be balanced and synchronized with the pressure of the outer pressurizing fluid in the pressure chamber 170 so as to allow the flexible channel 144 to achieve higher pressure than otherwise possible. For example, whereas an internal channel pressure of 1000 psi will burst a given channel when there is no external pressure; by maintaining an external channel pressure that is not less than 1000 psi more than the internal channel pressure, the internal channel pressure can be elevated to pressures significantly greater than 1000 psi. Furthermore, the sample chamber 140 can be pressurized by mobile phase pump 128 such that the sample chamber wall 142 goes into a tensile state of stress prior to being compressed by the working pressurizing fluid in pressure chamber 170, so as to allow maximum sample chamber deformation without subjecting the sample chamber to permanent deformation.

Further aspects of the invention contemplate utilizing walls 142 constructed in segments to allow or facilitate removal of certain segments as cartridges.

Temperature and pressure can be coordinated to achieve full thermodynamic control of enzymatic activity, binding affinity, or other chemical reactions.

A first fixture 152 can be utilized to secure a first end of chamber 140 in a first bracket 154 and a second fixture 156 can be utilized to secure a second end of chamber 140 in a second bracket 158. First bracket 154 can also be configured to receive and have secured therein an inlet port 162 and an outlet port to pressure transfer cell 104. Threaded interfaces can be utilized to secure any of fixtures 152 and 156, inlet port 162, and outlet port 164 to brackets 154 and 158. Particularly preferred configurations can involve configurations of fitting 164 that can interface or connect with an inlet of at least one component of the one or more analytical trains 102.

In accordance with one or more preferred configurations, the volume of sample mixture to be pressurized can be less than about 1 mL, in some cases, less than about 0.1 mL, in other cases, less than about 0.01 mL, and in still other cases, less than about 0.001 mL. In still other configurations, the volume of the sample mixture to be pressurized can be 0.0001 mL to about 1 mL, in some cases, 0.001 mL to 0.1 mL, and in still other cases, 0.01 mL to 0.1 mL. Further configurations can involve pressurizing sample mixtures of 0.0001 mL (0.1 µL), 0.001 mL (1 µL), 0.005 mL (5 µL), or even 0.01 mL (10 µL).

Multiple pressure transfer cells can be connected, in parallel or in series, that facilitate combinatorial or sequential operations or reactions, wherein at least one reaction step is pressure-sensitive. Multiple sample chambers can be interconnected so portions of sample mixtures can be transferred from one sample chamber to another sample chamber to undergo a subsequent treatment prior to being introduced into the analytical train 102. Combinatorial synthesis of oligonucleotides (including preparation of constructs), peptides, and other organic compounds can be performed in this manner.

In accordance with further embodiments of the invention, at least a portion of an inner surface of wall 142 can comprise pendent moieties that can bond to one or more target species or ligands.

In the exemplary embodiment illustrated, pressure transfer cell 104 further comprises a pressure chamber 170, defined by pressure wall 172, which encloses at least a portion of deformable channel 144. Pressure chamber 170 is typically connected to one or more sources 180 (FIG. 1) of a pressurizing fluid, or working fluid. As exemplarily illustrated in the embodiment of FIG. 2, pressure chamber 170 is configured as a pressure channel surrounding flexible channel 144. Where advantageous, a working fluid inlet port 182 can be utilized to introduce pressurized fluid into pressure chamber 170; and a pressure transducer port 190 can be utilized to measure the pressure in pressure chamber 170.

Commercially available pressure transducers that can be utilized include, for example, those manufactured by Honeywell Sensotec (USA).

The actual pressure within the sample chamber 170 can alternatively or additionally be measured by an in-line pressure transducer 139 such as the DF2 pressure transmitter from DJ Instruments, Inc., Billerica, Mass.

Figure 4:
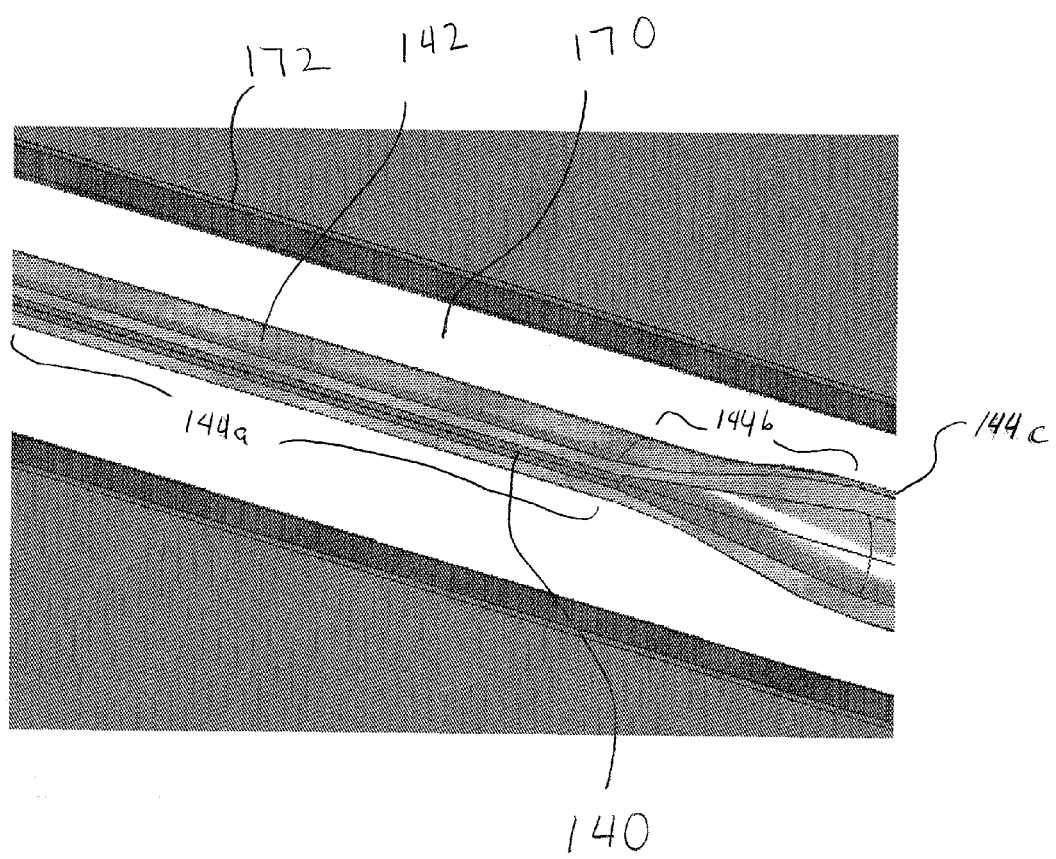
FIG. 4 is an exploded cross-sectional view of a portion of the flow path of a pressure transfer cell in accordance with one or more embodiments of the invention wherein a deformable channel has deformed by pressure of a pressurizing fluid in the surrounding, pressure chamber.

As shown in FIG. 4, where the sample chamber 140 is subjected to the pressure of a working fluid in the pressure chamber 170, the flexible wall 142 deflects to impart a pressure on the sample mixture contained therein. In one embodiment, the deflection of the wall 142 may result in a portion 144a of the channel 144 being flattened or compressed relative to other portions of the channel. This deformation may be due to portions of the channel (e.g., terminal end portion 144c) being thicker than other portions (e.g., central portion 144a) of the channel, or by portions of the channel (e.g., central portion 144a) being pre-stressed so as to deflect or deform in a determined manner, as described in more detail with respect to FIGS. 5-6.

As illustrated in FIG. 5, in one embodiment of the present invention, the sample chamber 140 of a pressure transfer cell 104 can include a filler rod 501, a pair of reinforcing segments 502 (only one of which is shown in FIG. 5), and sample chamber wall 142. The filler rod 501 may be formed from a substantially incompressible material such as stainless steel, and may extend along the length of the channel 144. Each of the pair of reinforcing segments 502 is formed from a rigid and preferably inert material and is disposed at each of the terminal ends of the channel 144. The sample chamber wall 142 is formed from a flexible or deformable material such as a polymeric material such as PEEK or FEP, a metallic material such as stainless steel, titanium alloys, or superelastic NiTi alloys, and is preferably inert, nonbinding, hydrophilic, or hydrophobic. As shown, a proximal end of the channel 144 includes a substantially circular terminal end portion 144c, a transitional portion 144b, and an ellipsoidal central portion 144a. Although not shown in FIG. 5, the distal end of the channel is similar to the proximal end of the channel, such that the ellipsoidal central portion 144a of the channel extends to a transitional portion and then to a substantially circular terminal end portion at the distal end of the channel 144. Although not shown in FIG. 5, the pressure wall 172 (FIG. 2) is disposed about the sample chamber 140. In use, the reinforcing segments 502, which do not extend into the ellipsoidal central portion 144a of the channel 144 help to maintain a circular geometry at the terminal ends of the pressure transfer cell and permit the fixtures 152, 156 (FIG. 2) to form a fluid tight seal at the terminal ends of the pressure transfer cell 104 by compressing the pressure wall 172 against the terminal end portions 144c of the channel.

FIG. 6 is a cross-sectional view of the sample chamber 140 of FIG. 5, without the filler rod 501 in place. As shown, the reinforcing segment 502 does not extend into the ellipsoidal central portion 144a of the channel 144. Preferably, the ellipsoidal central portion 144a of the channel 144 comprises approximately 50% to about 90% or more of the total length of the pressure transfer cell.

It should be appreciated that the ellipsoidal geometry of the central portion 144a of the channel 144 permits the channel to deform in a predictable manner and thereby pressurize the sample mixture contained therein. The ellipsoidal geometry of the central portion also reduces the amount of pressure needed to deform the channel, in comparison to a channel that is round throughout its length. The ellipsoidal central portion may be formed by either a permanent (i.e., plastic) deformation of the channel wall 142, such as by flattening a metal tube defining the channel 144, or by a temporary (i.e., elastic) deformation of the channel wall 142. For example, where the channel wall 142 is formed from an elastic material, the channel 144 may be disposed in a perforated plastically deformed metal tube to create an out-of-round condition so as to destabilize the channel 144 so that deformation may take place in a defined region and at lower pressures.

Non-limiting examples of sources of pressurizing fluid include those commercially available instruments that can provide pressurized fluids at least 1,000 psi, and up to about 60,000 psi, such as the HUB 440 pressure generator from Pressure BioSciences, Inc., South Easton, Mass. Higher pressure, up to over 100,000 psi can be used as needed for the application.

The various apparatus of the present invention can be utilized to modify and/or control activity or characteristics of a sample or components thereof. For example, the various systems and techniques of the present invention can facilitate nucleic acid sequencing, nucleic acid synthesis, protein sequencing, enzymatic chiral synthesis, and enantiomeric purification of racemic mixtures. Non-enzymatic reactions can also be controlled by utilizing one or more aspects directed to the various systems and techniques of the present invention. Desired effects of pressure upon the components of the sample mixture may include, for example, protein unfolding, protein folding, reversible inhibition of enzymatic activity, activation of enzymatic activity, and shifts in the reaction rate and the thermodynamic equilibrium of non-enzymatic reactions. Pressure-induced (or pressure controlled) inhibition includes inhibiting a single enzymatic reaction step, several sequential enzymatic reaction steps, or the complete enzymatic event. Furthermore, an inhibitory pressure can synchronize the activity of individual reactant molecules, e.g., enzyme, cofactor, or first or second substrate. When the pressure is changed to a permissive pressure, multiple enzyme molecules begin to act at more or less the same time, resulting in more uniform, accurate, and reproducible control of enzymatic activity. A molar excess of enzyme to substrate, if any, usually increases synchronous behavior. Enzymatic reaction steps include the mechanistic steps involved in the reaction between an enzyme (E) and a substrate (S) to form a product (P). Depending on the complete enzymatic event, these steps include conformational change of E, S, P, and combinations thereof; association or dissociation of E-S and E-P; interaction between cofactor and either S or E; interaction among S, E, and a cofactor; solvent interaction with E, S, or a cofactor; proton exchange between E and a component of the sample mixture, such as S, a solvent, or a cofactor; and a catalytic interaction between E and S. Depending on the enzymatic event, there can be more than one substrate (S, S', S" and so on), more than one product (P, P', P''' and so on), and more than one cofactor. Furthermore, some embodiments use more than one solvent or solute, e.g., salt or metal ion, and temperature in conjunction with pressure to provide inhibitory or permissive conditions which control an enzymatic reaction step.

Similarly, changing the pressure of the sample mixture to a pressure which can permit an enzymatic reaction step to occur can result in the occurrence of a subsequent enzymatic reaction step, a series of enzymatic reaction steps, or one or more complete enzymatic events. The various systems and techniques of the present invention can be utilized to control enzymatic activity by programming the desired series of single enzymatic events. For example, hyperbaric treatment that causes many biological macromolecules such as proteins, enzymes, antibodies, and polynucleotides to unfold or denature, which naturally function at pressures of 1 atmosphere. Such unfolding can effect inhibition of enzyme activity. Further, some enzymes or proteins, in particular those which naturally function at high pressures, e.g., in deep sea vent organisms, can be inhibited at lower pressure conditions.

The concentrations, buffers, solvents, enzymes, substrates, and other additives or facilitating molecules utilized in the various approaches of the invention may be utilized. Where advantageous, higher than usual concentrations of enzyme can be present to achieve more uniform and reproducible results. Those in the art are familiar with commercial sources for nucleic acids, markers, linkers, primers, buffers, amino acids, protecting groups, solvents, enzymes, and other related reagents, e.g., Aldrich, Milwaukee, Wis.; Pharmacia Biotech, Piscataway, N.J.; Promega Corp., Madison, Wis.; Sigma-Aldrich, St. Louis, Mo.; and Stratagene, La Jolla, Calif.

Applied hydrostatic pressure by, for example, pressure cycling, can be used to alter mutual solubility or miscibility of solvents in mixtures, e.g., azeotropic mixtures, solutions, suspensions, or multi-phase mixtures; to control the arrangement of molecules in micelles, emulsions, gels or colloids; and/or to control the dissolution of one or more components of the multi-phase mixture in another component or solvent. The various systems and techniques of the present invention can thus utilize changes in pressure to effect changes in mutual solubility of the components and depressurization of the system and, in some cases, can cause the mixture to break into multiple phases, thereby separating molecules into separate phases based upon the physiochemical properties.

Further, the various systems and techniques of the present invention can involve hydrostatic pressure to facilitate preparation of colloids or nanomaterials by dissolving components in one solvent, mixing the first solvent with another solvent, thereby leading to the formation of immiscible multi-phase mixtures when the first solvent is under atmospheric pressure. Pressure can also be used to control the size of micelles in a multi-phase system or emulsion to alter its physical property or stability.

The pressure can be applied as, e.g., hydraulic or pneumatic pressure.

A pressure cycle is the summation of exposing a sample to more than one pressure for a period of time at each pressure, e.g., raising the pressure and lowering the pressure, e.g., up from a first pressure to a second pressure and then down from the second pressure to a third pressure. Further, a second pressure cycle can be carried out, e.g., from the third pressure to a fourth pressure to a fifth pressure, and so forth. This process can be repeated. For example, a pressure cycle can consist of exposing a sample mixture, e.g., the mixture being exposed to pressure cycles, which typically has one or more components of interest, to a first pressure for a first period of time; exposing the sample mixture to a second pressure for a second period of time; and then exposing the sample mixture to a third pressure for a third period of time. There is no limit to the number of pressurization events that the sample can be exposed to, and the period of time spent at each pressurization event can vary and need not have the same duration.

Examples of pressure cycles are illustrated. A sample mixture, or at least a portion thereof, can be exposed to a first pressure for a period of time, $t_1$. The sample mixture, or at least a portion thereof, can then be exposed to a second pressure for a period of time, $t_2$. The sample mixture, or at least a portion thereof, can then be exposed to a third pressure for a period of time, $t_3$. The sample mixture can thus be exposed to various pressures for various periods of time $(t_n)$. The aggregation of each of these exposures to each pressure for each period of time may be considered as a pressure cycle. In some configurations of the present invention, the sample mixture can be exposed to a pressure that is greater than the first or second pressures for a period of time. Exposure to this pressure can, for example, introduce one or more reagent into the sample mixture being exposed to the pressure cycle by, for example, rupturing a secondary container containing such one or more reagents.

The pressure involved in the various systems and techniques of the present invention can be between about 100 MPa to about 1,000 MPa, e.g., about 100 MPa to about 900 MPa, about 200 MPa to about 800 MPa, about 300 MPa to about 700 MPa, about 400 MPa to about 600 MPa, about 100 MPa to about 350 MPa, about 250 MPA to about 500 MPa. For example, the maximum pressure can be from about 15 to about kpsi (35 kpsi=235 MPa), or about 80 kpsi (537 MPa), or about 30 kpsi, or about 240 MPa.

The minimum pressure involved in the various systems and techniques of the present invention can be between about 133 Pa to about 200 MPa, e.g., about 150 Pa to about 150 MPa, about 200 Pa to about 100 MPa, about 350 Pa to about 75 MPa, about 500 Pa to about 50 MPa, 750 Pa to about 35 MPa, about 1 MPa to about 25 MPa, about 1 KPa to about 1 MPa, about 25 KPa to about 250 KPa, about 50 KPa to about 500 KPa, about 100 KPa to about 300 KPa, about 250 KPa to about 750 KPa, about 1 MPa to about 100 MPa, about 25 MPa to about 200 MPa, about 50 MPa to about 100 MPa, about 100 MPa to about 200 MPa, about 135 Pa to about 500 Pa, about 150 KPa, about 100 MPa. In some embodiments, the minimum pressure used is atmospheric pressure at sea level, e.g., about 100 KPa, e.g., 101.3 KPa.

In some embodiments of the present invention, the maximum and minimum pressures utilized can be based on providing a minimum or maximum difference in pressure values. For example, the minimum and maximum pressures differ by no more than 200 MPa. As another example, the minimum and maximum pressures differ by no less than 100 KPa.

The number of pressure cycles, e.g., the number of times the applied pressure is raised and subsequently lowered, or the number of times the applied pressure is changed from a first value to a second value to, in some cases, a third value, which can be lower than the second value, that can be utilized in the present invention can vary. For example, the number of pressure cycles can range between about 1 cycle to about 1000 cycles, e.g., from about 5 cycles to about 800 cycles, from about 10 cycles to about 500 cycles, from about 20 cycles to about 250 cycles, from about 30 cycles to about 150 cycles, from about 50 cycles to about 100 cycles, from about 100 to about 300 cycles, from about 200 to about 400 cycles, from about 50 to about 150 cycles, from about 5 to about 35 cycles, from about 10 to about 25 cycles. In some embodiments of the present invention, the pressure cycles from a first pressure to a second pressure, which can be higher than the first pressure, to a third pressure, which can be lower than the second pressure; the third pressure may not be the same as the first pressure. In such embodiments, all three or more pressures are considered as being part of the pressure cycle.

The length of the pressure cycles, which is typically the total amount of time spent in the cycle, i.e., the amount of time spent at the first pressure plus the amount of time spent at the second pressure, plus the amount of time spent at any additional pressure conditions, e.g., at a third pressure, a fourth pressure, etc., can also be varied to implement one or more of the various aspects of the present invention. The length of the pressure cycle may be from about 5 seconds to about 60 minutes, e.g., about 10 seconds, about 20 seconds, about 30 seconds, about 45 seconds, about 60 seconds, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 15 minutes, about 20 minutes, about 25 minutes, about 30 minutes, about 35 minutes, about 40 minutes, about 45 minutes, about 50 minutes, about 55 minutes, about 60 minutes. In many embodiments, the length of time at the first and second pressures can be the same. For example, in an about a 20 second cycle, the sample mixture can be at the first pressure for about 10 seconds and at the second pressure for about 10 seconds.

The length of time spent at a given pressure condition, event, or level, e.g., at the first or second or third pressure, can be from about 5 seconds to about 30 minutes, e.g., about 10 seconds, about 20 seconds, about 30 seconds, about 45 seconds, about 60 seconds, about 2 minutes, about 3 minutes, about 4 minutes, about 5 minutes about 6 minutes, about 7 minutes, about 8 minutes, about 9 minutes, about 10 minutes, about 11 minutes, about 12 minutes, about 15 minutes, about 20 minutes, about 25 minutes, about 30 minutes. In several embodiments of the present invention, the length of time at the first and second pressures is the same. For example, in an about a 20 second cycle, the sample mixture can be at the first pressure for about 10 seconds and at the second pressure for about 10 seconds.

The exposure to a particular pressure condition, event, or level may be varied based on several considerations such as, but not limited to, the properties of any solvents and composition of the plurality of components in the sample mixture. The length of time spent at one pressure may be longer than the time spent at the other pressures. In some embodiments of the present invention, the sample mixture may be at each pressure for a different amount of time. For example, the sample mixture can be at the first pressure for about 10 seconds and at the second pressure for about 30 seconds.

Further non-limiting examples of pressure cycles are as follows:

Start at the atmospheric pressure at sea level (101.3 KPa), followed by 100 MPa held for 5 seconds and 30 seconds held at the atmospheric pressure at sea level (101.3 KPa), 20 cycles;

Start at the atmospheric pressure at sea level (101.3 KPa), followed by 20 seconds at 240 MPa and 20 seconds at the atmospheric pressure at sea level (101.3 KPa), 50 cycles; and Start at 100 MPa, followed by 413 MPa held for 10 seconds followed by 200 MPa held for 10 seconds followed by 100 MPa held for 10 seconds, the sequence repeated over 10 cycles.

In some embodiments involving three pressures in the cycle, the length of the pressure cycle is the total amount of time spent at the first, second, and third cycles.

Examples of pressure cycling parameters include: five one-minute cycles at 35 kpsi, where pressure is kept at 30 seconds at 241 MPa, followed by 30 seconds at approximately 101.3 KPa (atmospheric pressure); 20 cycles where a pressure of 100 MPa held for 5 seconds and atmospheric pressure (101.3 KPa) held for 30 seconds within each cycle; 30 cycles where pressure is maintained at 500 MPa for 10 seconds, followed by the step at 200 MPa for 20 seconds, which is then followed by 30 seconds at 100 MPa, resulting in a 1 minute for each pressure cycle.

Various temperatures at which one or more of the pressurization events are performed can also be utilized. Temperature can increase the disorder of samples, e.g., biological membranes, and facilitate the separation, release, or extraction of a molecular entity, e.g., component, of interest.

For example, various sample conditioning techniques of the present invention can be performed at between about −40° C. to +100° C., e.g., from about −20° C. to about 70° C., from about 0° C. to about 50° C., from 4° C. to about 37° C., from about 10° C. to about 30° C., from about 15° C. to about 25° C., at about 20° C., at about 23° C., at about 25° C., at about 70° C., or at about −2° C.

The choice of temperature for use in accordance with one or more embodiments of the invention can be dependent on the properties of any solvents and sample components of interest. The temperature can be altered, e.g., increasing or decreasing, in about 1° C. increments per unit time. The temperature at which the method is carried out can be regulated, e.g., by a circulating water bath, or by utilizing thermoelectric devices such as heaters 137 and Peltier coolers.

Various aspects of the present invention can also be performed by utilizing varying temperature and pressure conditions within each cycle to advantageously utilize changes associated with mutual solubility of solvents and sample components at various temperature and pressure conditions. For example, at the first pressure in the cycle, the sample mixture can be at a first temperature; at the second pressure of the cycle, the sample mixture can be exposed at a second temperature. In some embodiments, the first temperature is higher than the second temperature. In other embodiments, the second temperature is higher than the first temperature.

A variety of liquids can be used in the liquid phases of the various systems and techniques of the present invention. For example, solvents, detergents, buffers, chaotropic agents, e.g., chaotropic salts, and mixtures thereof can be used.

A variety of solvents can be employed in accordance with one or more aspects of the present invention. For example, the one or more solvents can be aqueous, organic, or lipid. The solvent system can thus form multi-phase mixtures, e.g., of poorly miscible reagents. For example, the solvent system can be biphasic or triphasic.

In some embodiments, at least two solvent phases, e.g., liquid phases, can be used, with at least two solvent phases that are not mutually miscible at one of the pressures of the pressure cycle, e.g., the solvent phases are not mutually miscible at the first pressure. Upon pressure cycling, the two solvent phases can become at least partially mutually miscible and, in some cases, partially mutually soluble, at the other pressure, e.g., at the second pressure, such as where the second pressure is greater than the first pressure. Upon return to the first pressure, or transition to a third pressure, typically at lower than the second pressure, the partial mutual miscibility is removed and the solvent phases typically separate. In some embodiments of the present invention, depending on the choice of solvent phases used, the solvent phases can become fully miscible (and in some cases, fully soluble) at the second pressure.

Protic or aprotic solvents may also be utilized. Examples of protic solvents include water, methanol, ethanol, formic acid, hydrogen fluoride, and ammonia. Examples of aprotic solvents include dimethyl sulfoxide, dimethylformamide, hexamethylphosphorotriamide, and mixtures thereof. Non-limiting examples of solvents include acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethyl ether, diethylene glycol, diglyme (diethylene glycol dimethyl ether), 1,2-dimethoxy-ethane (glyme, DME), dimethylether, dimethyl-formamide (DMF), dimethyl sulfoxide (DMSO), dioxane, ethanol, ethyl acetate, ethylene glycol, glycerin, heptane, hexamethylphosphoramide (HMPA), hexamethylphosphorous triamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, water, heavy water ($D_2O$), o-xylene, m-xylene, p-xylene, and mixtures thereof. Further non-limiting examples of solvents that may be utilized in various aspects of the present invention include chloroform, tetrachloroethylene, methanol, isopropanol, ethanol, water, aliphatic hydrocarbons, e.g., hexane and heptane, acetonitrile, formic acid, trifluoroacetic acid, glycerol, a lipid, e.g., triglyceride, phospholipid, sphingolipid, glycolipidsoil, e.g., from a sample itself, e.g., from a biological membrane, e.g., lipid membrane; lipid bilayer, or aqueous solution, e.g., a liquid component(s) that originates from the sample itself, e.g., from a biological membrane or cytoplasm, a fluorocarbon, other halocarbon, dimethyl sulfoxide (DMSO), fluorinated alcohols, e.g., amphiphilic fluorinated alcohols, e.g., 1,1,1,3,3,3-hexafluoro-2-propanol (HFIP), 2,2,2-trifluoroethanol (TFE), 2-fluoroethanol, 2,2,3,3-tetrafluoropropan-1-ol, 1.3-difluoropropan-2-ol, perfluorooctanol, other alcohols, and mixtures thereof. In some embodiments, a sample, e.g., the source of components, provides, e.g., functions as, a solvent. In some cases, this solvent from the sample constitutes one of the liquid phases of the extraction system. For example, in the extraction of a membrane protein, under appropriate conditions, the lipid bilayer acts as a solvent and as a liquid phase in the extraction method, e.g., the membrane protein is dissolved in the lipid bilayer.

As noted, mixtures of any of the solvents described herein can also be used.

The concentrations of the solvent can be tailored to particular requirements. Non-limiting examples of concentrations of solvents that may be utilized in the various aspects of the present invention include: about 0.2M HFIP; about 0.05M HFIP; about 0.38M to about 0.57M HFIP; about 60% HFIP; about 75% HFIP; about 95% HFIP; about 100% HFIP; about 1% to about 5% formic acid. The solvents can be made up in various other solvents, e.g., acetonitrile, or buffers, e.g., phosphate buffered solution (PBS). The solvents can be used by themselves to constitute a phase in the methods described herein. Alternatively, a solvent, e.g., a solvent listed herein, can be a solvent that, along with another component, e.g., a liquid, e.g., another solvent, make up one solvent phase. For example, 50% acetonitrile with 0.1% formic acid can make up on solvent phase, as illustrated in the examples herein.

A single solvent phase can include a combination of solvents. For example, a solvent phase can be chloroform: methanol:water in a 2:5:2 or 4:4:1 (w:w:w) ratio; or methanol:chloroform in a 1:1 (w:w) ratio. As another example, 50% acetonitrile with 0.1% formic acid can be used as a solvent phase.

The solvents can include an azeotrope, or an azeotrope can form when solvent phases are exposed to one or more pressurization events in accordance with some aspects of the present invention. Thus, where azeotropic mixtures that can act as different solvents by exhibiting altered solubility and ability to dissolve other compounds, such azeotropic solvent systems can be implemented to effect one or more features of the present invention. Hydrostatic pressure can alter the properties of azeotropic solvent mixtures as it alters properties of individual solvents. Non-limiting examples of azeotropes that can be implemented in the present invention include 95.5% ethanol and 4.5% water (w:w); 20.2% hydrogen chloride and 79.8% water (w:w); 1.2% water and 98.8% diethyl ether (w:w); 20% acetone and 80% chloroform (w:w); 30% acetone, 47% chloroform, and 23% methanol (w:w:w).

In some embodiments, one or more solvents can be added to a sample mixture to facilitate the formation of two or more liquid phases. For example, the addition of a solvent, e.g., an amphiphile such as HFIP, to a sample that contains one or more hydrophilic and/or polar components and one or more lipids can result in the formation of stable mixtures with the one or more hydrophilic and/or polar components and the one or more lipids, e.g., upon exposure to an increased pressure level. When pressure is decreased, the one or more hydrophilic and/or polar phases, e.g., HFIP, and one or more lipids separate into two or more liquid phases, e.g., thereby leading to the separation of components into the hydrophilic and/or polar or lipid phases, e.g., leading to the separation of a component of interest. In some embodiments of the invention, one solvent can be added to a sample mixture, which can effect the formation of two or more liquid phases, e.g., the sample provides a solvent(s), e.g., liquid phase. The addition of a solvent, e.g., an amphiphile such as HFIP, to a sample mixture that contains water and lipids can result in the formation of stable mixtures with water and the lipids, e.g., upon exposure to an increased pressure level. When pressure is decreased, the water, e.g., and HFIP, and lipids separate into two or more liquid phases, e.g., thereby leading to the separation of components into the water and lipid phases, e.g., leading to the separation of a component of interest.

In some embodiments, an organic solvent, e.g., a volatile organic solvent, e.g., HFIP, may need to be removed. For example, the removal of a volatile organic solvent can be accomplished by evaporation. In some embodiments, the removal of the volatile organic solvent can be accomplished by precipitation of the component(s) of interest. Subsequently, remaining solvent can be separated from the resulting pellet. Precipitation can be accomplished from a solvent, e.g., HFIP, by the addition of the appropriate component, e.g., an aqueous solution. Precipitation efficiency can be modified by sample concentration, temperature, pH, time, pressure, and the addition of other solutes, e.g., salts, chaotropic agents, detergents, or other components.

A variety of buffers can be used with the various systems and techniques described herein. For example, PBS can be used in a solvent phase of the methods. A wide variety of buffers can be used to maintain a desired pH of an extraction solvent and to maintain the solubility of desired components in a particular solvent and compatibility with a subsequent analytical method. Examples of such buffers include HEPES, TRIS, MES, ammonium bicarbonate, ammonium acetate, formic acid, trifluoroacetic acid, acetic acid, etc.

Various concentrations of salts can be used to control osmotic pressure in accordance with one or more aspects of the present invention. For example, a 0.9% sodium chloride can be used in the preparation or conditioning of components from mammalian cells. Osmotic pressure that can act synergistically with hydrostatic pressure can be utilized during pressure cycling in accordance with the present invention. For example, hypotonic concentrations of salts in the extraction solution can result in cell swelling and can act synergistically with the pressure cycling treatment to disrupt cellular plasma membranes. Conversely, hypertonic salt concentrations can be used to protect cells from disruption at certain pressure cycling conditions. For mammalian cells, NaCl concentrations below about 0.9% are typically hypotonic, and concentrations above about 0.9% are typically considered hypertonic.

One or more detergents or chaotropic agents, e.g., chaotropic salt, can be added to a solvent phase in accordance with one or more aspects of the present invention. In some embodiments, the amount of detergent used can be less than the amount used for known partitioning techniques, such as techniques based on mechanical shaking. In some embodiments, when a detergent is used in the methods described herein, no foaming is formed during the extraction. Non-limiting examples of detergents that can be used in one or more embodiments of the present invention include anionic detergents, e.g., SDS, Cholate, Deoxycholate; cationic detergents, e.g., C16TAB; amphoteric detergents, e.g., LysoPC, CHAPS, Zwittergent 3-14; and non-ionic detergents, e.g., Octylglucoside, Digitonin, C12E8, Lubrol, Triton X-100, Nonidet P-40, Tween 80. Several amphiphylic organic solvents, such as fluorinated alcohols, such as HFIP, TFE, perfluorooctanol, etc., can be regarded as possessing detergent functionality. Such solvents can be used alone or in combination, as an additive to other solvents and buffer systems, e.g., solvent and buffer systems described herein. The concentration of detergent used can be, for example, from about 0.001% to about 10%, e.g., about 0.1% to about 2%, e.g., about 0.5% to about 4%, e.g., about 1% to about 2%. However, in some embodiments of the present invention, the sample mixture can be free or substantially free of a detergent.

As noted, one or more chaotropic agents can also be used. Examples of such agents include urea, guanidinium chloride, guanidinium isothiocyanate, and guanidine hydrochloride. The concentration used can be about 0.1M to about 8M. Examples of chaotropic agents include those described, e.g., in U.S. Pat. No. 7,064,192 and U.S. Patent Application Publication Nos. 2006/0188970, 2004/0038333, 2003/0083475, and 2002/0137157.

Additional reagents may also be utilized. For example, one or more enzyme inhibitors, e.g., one or more of protease inhibitors such inhibitors of serine, cysteine, and aspartic proteases, and aminopeptidases, 4-(2-aminoethyl)benzenesulfonyl fluoride (AEBSF), pepstatinA, E-64, bestatin, leupeptin, and aprotinin, DNAse inhibitors, aurintricarboxylic acid, RNAse inhibitors, diethylpyrocarbonate (DEPC), Cesium Trifluoroacetate (CsTFA), recombinant placenta RNAse inhibitor, SUPERASE•INT™, ANTI-RNase or RNASECURE™ (Ambion), SCRIPTGUARD™ (Epicentre Biotechnologies), DEPC, metal chelating agents (e.g., DTPA, EDTA, EGTA, NTA, desferal) can be utilized to stabilize a component of interest.

Mineral oil can also be utilized to improve band sharpness and intensity. Other agents that effect improved phase separation which allows for efficient partitioning of endogenous lipids in a sample into the oil layer during centrifugation may be utilized.

High concentrations of salts that affect the extent of precipitation of certain proteins may also be utilized to effect interference with or to promote protein precipitation. Typically, endogenous sample-derived salts are insufficient to cause any significant effects upon precipitation. In many instances, exogenous salts can be added to improve total protein precipitation. In addition, optimized salt concentrations can be used to selectively precipitate desired proteins and retain undesired proteins in the supernatant and vice versa. For example, such an approach can be used to deplete a complex sample of highly abundant protein species, e.g., serum albumin, immunoglobulins, etc., and enrich for the low abundance proteins of biological significance.

The systems and techniques described herein can be performed alone or in combination with one or more additional steps/methods to facilitate, for example, isolation of a component of interest. The one or more additional steps can be performed before or after one or more pressurization events. For example, centrifugation, e.g., gradient centrifugation or ultracentrifugation or centrifugation in the same vessel, precipitation or precipitation of one or more sample components, immunoprecipitation to remove a contaminant, permeablization of a cell, with or without a detergent, using hypotonic buffer conditions to disrupt the plasma membrane or other membranes surrounding organelles, enrichment for a particular tissue, cell or organism type, membrane fraction, etc.; fractionation of sample constituents according to their localization in the cell or tissue or according to their physiochemical properties, e.g., electrostatic charge, hydrophobicity, solubility in a particular solvent, molecular conformation or binding affinity, etc., can be performed along with an extraction method provided herein to improve the isolation or purification of a component of interest.

The pressure cycling protocols, e.g., temperatures, pressures, periods, solvents, salts, agents, and buffers can be empirically determined.

The systems and techniques of the present invention can be used to extract or separate one or more components of interest from a sample mixture. Non-limiting examples of sources upon which the present invention may be utilized include biological and synthetic, e.g., man made, sources. Examples of sources of biological origin include mammalian, e.g., human or domesticated animal, fungal, bacterial, viral, and plant sources. Examples of such sources include a cell, an organelle, e.g., mitochondrion, nucleus, Golgi apparatus, chloroplast, endoplasmic reticulum, vacuole, acrosome, centriole, cilium, glyoxysome, hydrogenosome, lysosome, melanosome, mitosome, myofibril, nucleolus, parenthesome, peroxisome, ribosome, microsome, vesicle, a membrane, e.g., a lipid membrane, e.g., a lipid bilayer, a biological sample (tissue sample (adipose tissue, liver, kidney, skin, pancreas, stomach, intestine, colon, breast, ovary, uterine, prostate, bone, tendon, cartilage, hair, nail, tooth, heart, brain, lung, skin, nerves, biopsy, etc.), blood, urine, milk, semen, saliva, mucus, other bodily fluids and solids)), collection of cells, e.g., blood, semen, mucus, saliva, tissue biopsy. Examples of other sources include butter, cream, a pharmaceutical or cosmetic formulation (ointment, lotion, cream, shampoo, conditioner, nanoparticle drug formulation, etc.), a pharmaceutical formulation in a tablet, capsule or gelcap form, a multi-phase composition such as emulsion or suspension of solid particles (ink, paint (e.g., latex paint), lacquer, lubricant, fuel, ingredients for chemical synthesis, etc.)), suspension of liposomes, membrane vesicles, liquid propellants, fuels, elastomers, polymers, ink formulations; emulsions of oil in water and other solvents such as industrial lubricants, soil, e.g., suspensions of soil samples, minerals, and so forth.

Examples of components, e.g., molecular entities, of the sample mixture include a protein, e.g., membrane bound protein, transmembrane protein, type I or type II membrane protein, receptor, enzyme, a lipoprotein, a glycoprotein, a polysaccharide, e.g., heparin or heparin-derived polysaccharide, starch, insulin, etc., a proteoglycan, e.g., collagen, chitin, murein, etc., a polyphenol, e.g., a tannin, a phenylpropanoid, e.g., a lignin, a flavonoid, a vitamin, a toxin, a pollutant, a lipid, e.g., phospholipids, e.g., phosphatidylcholine (PtdCho), phosphatidylethanolamine (PtdEtn), phosphatidylinositol (PtdIns), phosphatidylserine (PtdSer)), glycolipids, steroids, e.g., estrogen, progesterone, androgen, testosterone, ecdysteroids such as ecdysterone, corticosteroids such as glucocorticoids and mineralocorticoids, anabolic steroids, cholesterol, phytosterols, brassinosterols, ergosterols, a membrane (cell membrane, organelle membrane, lipid bilayer), a nucleic acid (DNA (nuclear DNA, mitochondrial DNA), RNA (mRNA, tRNA, rRNA, mtRNA, microRNA)), a virus, e.g., HIV, HPV, hepatitis A, B, C, D, E, F, or G, cytomegalovirus, Epstein-Barr virus, yellow fever, a bacterium, e.g., Gram positive or Gram negative bacteria, mutualist bacteria, pathogenic bacteria, a component present in a bacterial cell or in a cell of other microorganism or other cell type, e.g., a protein recombinantly produced by the bacterium, yeast or a mammalian cell, recombinant proteins contained within the inclusion bodies, bacterial DNA or RNA, an antigen, e.g., from a bacterium, fungal or mammalian cell or from a virus, a virus, e.g., for vaccine production, a pharmaceutical agent such as a small molecule, a metabolite, e.g., a small molecule metabolite, a pesticide, e.g., bactericide, fungicide, herbicide, insecticide, e.g., ovicide, larvicide or adulticide, miticide, molluscicide, nematicide, rodenticide, virucide, a drug, e.g., a pharmaceutical drug, a drug metabolite, a dye, a food constituent, a nanoparticle formulation, a lipid raft, an amyloid plaque, microtubule, cytosol, oils, terpenes, and other lipophilic compounds, e.g., from plant material, various compounds, e.g. alkaloids, flavonoids, isoflavons, proanthocyanidins, anthocyanins from plants, e.g., medicinal plants, food flavor constituents, e.g., capsaicin, from food preparations, lipid-soluble vitamins, e.g., tocopherols, carotenoids, lycopene, etc, from plant oils or animal fat, topical drug formulation constituents, e.g., from skin and underlying tissues, a particular cell type, polymer, elastomer, lubricant, pigment, plasticizer, and so forth. For example, extraction of membrane proteins from lipid-rich adipose tissue or extraction of enzymes such as cytochromes P450 from liver microsomal fraction is greatly simplified and higher yields of desired proteins are obtained.

Examples of cell types include blastomere, egg, embryonic stem cell, epithelial cell, erythrocyte, fibroblast, hepatocyte, leukocyte, myoblast, myotube, neuron, oocyte, osteoblast, osteoclast, sperm, T-cell, zygote (animal or plant), aleurone, collenchyma, endodermis, endosperm, epidermis, mesophylll, meristematic cells, palisade, parenchyma, phloem sieve tube, pollen generative, pollen vegetative, sclerenchyma, tracheids, xylem vessel. Also included are various types of keratinizing epithelial cells, wet stratified barrier epithelial cells, exocrine secretory epithelial cells, hormone secreting cells, gut, exocrine glands and urogenital tract cell, metabolism and storage cells, barrier function cells (lung, gut, exocrine glands and urogenital tract), epithelial cells lining closed internal body cavities, ciliated cells with propulsive function, extracellular matrix secretion cells, contractile cells, blood and immune system cells, sensory transducer cells, autonomic neuron cells, sense organ and peripheral neuron supporting cells, central nervous system neurons and glial cells, lens cells, pigment cells, germ cells, nurse cells.

Reactants can be used in various configurations of the systems and techniques of the present invention. The one or more sample chambers can have one or more subchambers (not shown) that contains one or more reagents. The one or more reagents can then be released and introduced into the sample mixture upon rupture of containment structures that confine the one or more reagents. Rupture and release of the one or more reagents can be initiated upon application of pressure by, for example, the pressurizing fluid.

Further configurations in accordance with one or more aspects of the present invention include restraint systems that allow separation or collation of components of a sample mixture by size, charge, polarity, chirality, or combinations thereof. Non-limiting examples of restraint systems comprise semi-permeable material such as a membrane or matrix. The semi-permeable material may occupy a complete cross-section of the sample chamber in the manner of a filter or net (not shown). The restraint, such as a semi-permeable barrier, can divide the sample chamber into two segments; more than one semi-permeable barrier will divide the sample chamber into more than two segments.

Further configurations in accordance with one or more aspects of the invention can involve the use of immobilized substrates within the sample chamber. Such immobilization systems can comprise at least one permeable, or semi-permeable, membrane, typically having pores which can allow one or more components of interest, e.g., enzyme and products or small molecules to pass through; and another membrane has pores which allow only products or small molecules to pass through. The semi-permeable material may be configured as a rigid or flexible pouch, bag, or envelope attached to a wall of the sample chamber. For example, a chamber can include a porous plastic or glass plug with an immobilized reactant or reagent (either enzyme or substrate); or a membrane support on an interior surface of the sample chamber which supports a porous membrane containing an immobilized reactant. Additional examples include a rigid, hollow porous frit containing an immobilized reagent, wherein the frit is attached to an interior surface of the chamber. In some embodiments, the restraint can be moved to provide a semi-permeable barrier and then temporarily removed during a programmed series of cycles to allow free flow of all components out of the sample chamber. Preferably, the separation material is generally chemically inert with respect to the sample mixture components and structurally resistant to fluid pressures as high as the inhibitory pressure(s) in a particular application. Size-discriminating membranes or films include DIAFLO™ ultrafilter membranes, available from Amicon, Beverly, Mass., which are commercially available in molecular weight cut-offs ranging from 0.5 to 300 kD. Membranes can be utilized to separate enzymes from free nucleotides or amino acids; and immobilized substrates from free enzymes and free nucleotides or amino acids in solution. A separation material such as a membrane or matrix may be impregnated, coated, or otherwise functionalized with a substance or covalently bonded ligand which can interact with a component of the sample mixture. Materials having asymmetric surface properties or asymmetric pore channel hydrophobicity, hydrophilicity, and/or size, may be used. The semi-permeable material can also include analogs of column chromatography, whereby chiral separations are achieved using packed materials through which at least one sample mixture component is eluted.

Depending on the reaction involved and the restrictive properties of the restraint selected, the fluid can include a nucleotide, an amino acid, an enzyme, an unbound enzymatic substrate, a cofactor, and various solvents or salts. Similarly, the components of the sample mixture can also include solvents, salts, enzyme, a free substrate, or an immobilized reagent. Immobilized reagents can include organic compounds attached to a non-liquid support.

Examples of a support include polymeric, composite, plastic, or glass beads, matrices, boards or other shapes, including cylinders or tubes.

In accordance with still further aspects of the invention, sample preparation train 101 can further comprise one or more sensors configured and disposed to detect or monitor at least one characteristic or condition of at least one of a subsystem or a component thereof. The detector or sensor can be in communication, wired or wirelessly, with controller 106. Thus, one or more components of apparatus 100 can be monitored, analyzed before, during, or after one or more pressurization operations. For example, pressure transfer cell 104 can comprise one or more pressure sensors 190 (FIG. 2) disposed to measure a pressure of a pressurizing fluid. Non-limiting examples of other types of detectors, monitors, or sensors include radioisotopic detectors, infrared spectrometers, mass spectrometers, gas chromatography-mass spectrometers, spectrophotometers, spectrofluorometers, electrochemical detectors, surface plasmon resonance detectors, pressure sensors, temperature sensors, position indicators, and photometers.

Analysis of the components of the sample mixture can be performed in the one or more analytical trains 102. For example, a component of interest, e.g., a phase containing a component of interest, that is purified using the methods described herein can be compatible with downstream processes, e.g., analytical methods such as those compatible with processes that are not compatible with detergents, and/or can be directly used in such processes. The one or more products containing the one or more components of interest from sample conditioning or preparation train 101 may or may not require further purification and may be directly compatible with certain methods of analysis, e.g., HPLC and/or LC/MS, GC and/or GC/MS, e.g., due to the absence of detergents, volatility of the solvents and ability to inject the resulting extract directly onto the HPLC column without prior solvent removal. Direct application of sample can minimize the potential loss of components of interest due to degradation or sample manipulation.

Thus, for example, analytical train 102 can comprise two-dimensional gel electrophoresis, one-dimensional gel electrophoresis, Western blotting, ELISA, protein or peptide mass fingerprinting, e.g., using MALDI-TOF/TOF, multidimensional electrophoresis, e.g., solution phase isoelectric focusing followed by two-dimensional gel electrophoresis of concentrated pI fractions, mass spectrometry (MALDI-MS, LC-MS/MS, MALDI-TOF MS, or LC-ESI-MS/MS), PCR, RT-PCR, and microarrays, thin-layer chromatography, liquid chromatography, e.g., HPLC, gas chromatography, GC/MS, electron microscopy, fluorescent microscopy, and surface analysis methods. In certain embodiments, isolated molecules or complexes thereof may be used in functional assays, e.g., enzymatic activity assays, in-vitro metabolism assays, etc., or subjected to subsequent fractionation or extraction steps.

Applications of the present invention can involve pressure-enhanced enzymatic digestion, e.g. proteolysis with trypsin, de-glycosylation with PHGase F (proteomics), removal of undesired protein by Proteinase K (genomics); sample preparation digestion for clinical proteomics, e.g. MRM assays for known biomarkers in plasma; chemical derivatization of samples for fluorescent detection, radioisotope and stable isotope labeling; on-line cell lysis for drug metabolism studies, high-content screening and metabolomics; lysis of bacterial cells for detection of extreme pathogens (minimized hazardous sample handling; fully automated, unattended detection systems for field chemical or biological warfare or environmental monitoring; and automated point-of-care diagnostics).

The controller 106 of the present invention may be implemented using one or more computer systems. The computer system may be, for example, a general-purpose computer such as those based on an Intel PENTIUM®-type processor, a Motorola PowerPC® processor, a Sun UltraSPARC® processor, a Hewlett-Packard PA-RISC® processor, or any other type of processor or combinations thereof. Alternatively, the computer system may include specially-programmed, special-purpose hardware, for example, an application-specific integrated circuit (ASIC) or controllers intended for analytical systems.

The computer system can include one or more processors typically connected to one or more memory devices, which can comprise, for example, any one or more of a disk drive memory, a flash memory device, a RAM memory device, or other device for storing data. The one or more memory devices can be used for storing programs and data during operation of the system 100 and/or the control system. For example, the one or more memory devices may be used for storing historical data relating to the parameters over a period of time, as well as operating data. Software, including programming code that implements embodiments of the invention, can be stored on a computer readable and/or writeable nonvolatile recording medium, and then typically copied into the one or more memory devices wherein it can then be executed by one or more processors of the controller 106. Such programming code may be written in any of a plurality of programming languages, for example, Labview, Java, Visual Basic, C, C#, or C++, Fortran, Pascal, Eiffel, Basic, COBAL, or any of a variety of combinations thereof.

Components of the controller may be coupled by an interconnection mechanism, which may include one or more busses, e.g., between components that are integrated within a same device and/or a network, e.g., between components that reside on separate discrete devices. The interconnection mechanism typically enables communications, e.g., data, instructions, to be exchanged between components of the controller.

The controller can also include one or more input devices, for example, a keyboard, mouse, trackball, microphone, touch screen, and one or more output devices, for example, a printing device, display screen, or speaker. In addition, the control system may contain one or more interfaces that can provide one or more indications or displays of the status or conditions of any of the various subsystems or components of system 100. Such interfaces can be a man-machine display apparatus 110. Other components of the controller provide connections to a communication network, in addition or as an alternative, to the network that may be formed by one or more of the components of the system.

According to one or more embodiments of the invention, the one or more input devices may include sensors for measuring parameters, such as pressure transducer connected to port 190 and to in-line pressure transducer 139. Alternatively, the sensors, the metering valves and/or pumps, or all of these components may be connected to a communication network that is operatively coupled to the controller. For example, sensors that monitor a position or orientation of any of apparatus 120 or valves 124, 132, and 134, e.g., open or closed, may be configured as input devices that are directly connected to the controller. Metering valves, pumps, and motors, such as actuator 122, may be configured as output devices that are connected to the controller, and any one or more of the above may be coupled to another computer system or component so as to communicate with controller 106 over a communication network. Such a configuration permits one sensor to be located at a significant distance from another sensor or allow any sensor to be located at a significant distance from any subsystem and/or the controller, while still providing data therebetween.

The controller can include one or more computer storage media such as readable and/or writeable nonvolatile recording medium in which signals can be stored that define a program to be executed by one or more processors. The medium may, for example, be a disk or flash memory. In typical operation, the one or more processors can cause data, such as code that implements one or more embodiments of the invention, to be read from the storage medium into a memory device that allows for faster access to the information by the one or more processors than does medium. The memory device is typically a volatile, random access memory such as a dynamic random access memory (DRAM) or static memory (SRAM) or other suitable devices that facilitates information transfer to and from the one or more processors.

The control system upon which various aspects of the invention may be practiced is not limited to being implemented in software, or on the controller. Indeed, rather than implemented on, for example, a general purpose computer system, the controller, or components or subsections thereof, may alternatively be implemented as a dedicated system or as a dedicated programmable logic controller (PLC) or in a distributed control system. Further, it should be appreciated that one or more features or aspects of the invention may be implemented in software, hardware or firmware, or any combination thereof. For example, one or more segments of an algorithm executable by the controller can be performed in separate computers, which in turn, can be communication through one or more networks.

EXAMPLE

This example illustrates a pressurizing sequence that may be implemented in accordance with one or more aspects of the invention.

a. Open inlet valve 132, close outlet valve 134 or 135.

b. Fill pressure transfer cell to moderate pressure via sample delivery train 103.

c. Close inlet valve 132.

d. Control system temperature if needed.

e. Control working fluid pressure to a desired or predetermined level to achieve desired sample pressure for a desired period of time.

Sample pressure can be measured by sensor 139 if valve 134 is not closed. Once working fluid pressure 180 needed to achieve desired sample pressure is known, valve 134 can be closed to remove sensor 139 from fatigue damage. This may or may not be needed depending on the magnitude of the sample pressure used.

f. Release working fluid pressure.

g. Open outlet valve 135, 134 and inlet valve 132.

h. Move sample fluid from sample conditioning train 101 into analytical train 102 by means of sample delivery train 103.

i. Analyze conditioned sample mixture.

Having now described some illustrative embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention. For example, some aspects of the invention can involve modification or retrofitting of existing autosamplers to include one or more sample conditioning trains disclosed herein. In particular, although many of the examples presented herein involve specific combinations of method acts or system elements, it should be understood that those acts and those elements may be combined in other ways to accomplish the same objectives.

Those skilled in the art should appreciate that the parameters and configurations described herein are exemplary and that actual parameters and/or configurations will depend on the specific application in which the systems and techniques of the invention are used. Those skilled in the art should also recognize or be able to ascertain, using no more than routine experimentation, equivalents to the specific embodiments of the invention. It is therefore to be understood that the embodiments described herein are presented by way of example only and that, within the scope of the appended claims and equivalents thereto; the invention may be practiced otherwise than as specifically described. For example, rather than having an annular configured pressurizing chamber 170 that is disposed about the sample chamber 140, the sample chamber can be disposed around a deformable, expandable pressurizing channel and contained within rigid wall 172. Pressurization of pressurizing fluid contained within the pressurizing channel expands the pressurizing channel, thereby increasing the applied pressure within annularly-shaped sample chamber.

Additionally, there is no essential requirement that the channel 144 be linear, for example a coil or bellows type channel may achieve the same purpose should a lager volume of sample fluid or channel surface area be required.

Further configurations can involve a plurality of serially connected pressure transfer cells, each having independently controllable pressurization subsystems. Such configurations can facilitate sequential pressure cycling events. For example, a first pressure transfer cell can pressurize the sample mixture pressurization condition to a first pressure, e.g., about 1 MPa. The sample mixture, or portions thereof, can then be transferred to a second pressure transfer cell wherein the sample mixture, or the portion thereof, can be pressurized to a second pressure, e.g., atmospheric or about 2 MPa. The sample mixture, or portions thereof, can then be transferred to a third pressure transfer cell, wherein the sample mixture, or the portion thereof, can be pressurized to a third pressure, equal to, less than, or greater than any of the first or second pressure. While the sample mixture is being pressurized in the second or third pressure transfer cell, or both, a second sample mixture can be pressurized in the first pressure transfer cell. Such sequential configurations can thus provide pressurization events in a semi-continuous manner, by utilizing a plurality of pressure transfer cells.

Moreover, it should also be appreciated that the invention is directed to each feature, system, subsystem, or technique described herein and any combination of two or more features, systems, subsystems, or techniques described herein and any combination of two or more features, systems, subsystems, and/or methods, if such features, systems, subsystems, and techniques are not mutually inconsistent, is considered to be within the scope of the invention as embodied in the claims. Further, acts, elements, and features discussed only in connection with one embodiment are not intended to be excluded from a similar role in other embodiments.

As used herein, the term "plurality" refers to two or more items or components. The terms "comprising," "including," "carrying," "having," "containing," and "involving,"

whether in the written description or in the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A flow-through sample preparation device comprising:
    a sample delivery train configured to provide a micro liter range liquid sample, the sample delivery train including an output valve;
    a sample conditioning train including a pressure transfer cell configured to pressurize the micro liter range liquid sample to a desired pressure of between about 2,000 psi and about 100,000 psi, the pressure transfer cell having an external source of a pressurized liquid,
        a pressure chamber fluidly connected to the external source of the pressurized liquid, and
        a flow-through sample chamber fluidly connected to the sample delivery train, the sample chamber being configured to isolate the micro liter range liquid sample during pressurization thereof, the sample chamber being disposed within the pressure chamber, the sample chamber having a wall, the wall being fabricated from a flexible or deformable material and configured to contain the micro liter range liquid sample, and
    a sample analysis unit,
    wherein, during operation, the pressure chamber is configured to apply pressure to the sample chamber such that the wall of the sample chamber is deflected to impart a pressure on the micro liter range liquid sample contained therein to promote conditioning thereof via modulating, facilitating, or effecting one or more reactions therein that can be at least partially pressure regulated by high pressure conditions and, subsequent to conditioning, the micro liter range liquid sample is fluidically passed to the sample analysis unit.

2. The device of claim 1, wherein the flexible or deformable material is a metallic material comprising stainless steel, a titanium alloy or a superelastic nickel titanium alloy.

3. The device of claim 1, further comprising a controller configured to adjust the pressure of the liquid sample within the sample chamber.

4. The device of claim 3, wherein the controller is further configured to adjust a temperature of the liquid sample within the sample chamber.

5. The device of claim 4, wherein the temperature of the liquid sample is adjusted within a range of about −40° C. to about 100° C.

6. The device of claim 4, wherein the controller is configured to coordinate temperature and pressure conditions to achieve thermodynamic control of enzymatic activity, binding affinity or other chemical reaction associated with the liquid sample within the sample chamber.

7. The device of claim 3, wherein the controller is further configured to provide an incubation period for the liquid sample within the sample chamber.

8. The device of claim 3, wherein the controller is configured to generate one or more control signals to: fill the pressure chamber with the pressurized liquid to moderate pressure therein, adjust the pressure of the pressurized liquid to a predetermined level to achieve a desired pressure of the liquid sample, release the pressure of the pressurized liquid to produce a conditioned sample mixture, open the outlet and/or an inlet valve, move the conditioned sample mixture to the inline sample analysis component, or analyze the conditioned sample mixture.

9. The device of claim 3, wherein the controller is configured to pressure cycle the pressure transfer cell to produce fluctuations in pressure applied to the liquid sample.

10. The device of claim 9, wherein pressure cycling involves repeatedly increasing and reducing the pressure of the pressurized liquid within the pressure chamber.

11. The device of claim 10, wherein a pressure cycle is based on a property of a solvent associated with the liquid sample or a composition of the liquid sample.

12. The device of claim 11, wherein the solvent comprises at least two solvent phases.

13. The device of claim 11, wherein the liquid sample comprises at least one salt, reagent or buffer.

14. The device of claim 9, wherein a pressure cycle ranges from about 4 seconds to about 30 minutes in duration.

15. The device of claim 14, wherein a length of time spent at any given pressure condition within the pressure cycle is from about 5 seconds to about 30 minutes.

16. The device of claim 9, wherein a pressure cycle comprises between about 1 and 1000 pressure conditions.

17. The device of claim 1, wherein the pressure transfer cell is configured to pressurize the liquid sample to a pressure of between about 2,000 psi to about 50,000 psi.

18. The device of claim 17, wherein the pressure transfer cell is configured to pressurize the liquid sample to a pressure of between about 2,000 psi to about 10,000 psi.

19. The device of claim 1, further comprising a separation apparatus fluidly connected upstream of the pressure transfer cell.

20. The device of claim 1, further comprising a cartridge trap configured to facilitate conditioning of the liquid sample upstream or downstream of the pressure transfer cell.

21. The device of claim 1, wherein a thickness of the wall of the sample vessel varies along a length of the sample chamber.

22. The device of claim 1, wherein at least a portion of the wall of the sample chamber is pre-stressed to deflect or deform in a predetermined manner.

23. The device of claim 1, wherein the wall of the sample chamber comprises at least one pendant moiety for binding to one or more target species or ligands.

24. The device of claim 1, wherein the sample chamber is characterized by an ellipsoidal geometry.

25. The device of claim 1, further comprising at least one filler rod within the sample chamber.

26. The device of claim 1, wherein the sample chamber includes an external brace.

27. The device of claim 1, wherein the device pressurizes a sample volume of between about 0.0001 mL to about 1 mL within the sample chamber during operation.

28. The device of claim 1, further comprising a second pressure transfer cell.

29. The device of claim 1, further comprising a first pressure transducer configured to measure a fluid pressure within the pressure chamber.

30. The device of claim 29, further comprising a second pressure transducer configured to measure a fluid pressure within the sample chamber.

31. The device of claim 1, wherein the pressure cell promotes protein digestion, cell lysis, pressure induced chemical reaction or pressure induced enzymatic reaction within the liquid sample.

* * * * *